(12) United States Patent
Toriumi

(10) Patent No.: US 9,714,865 B2
(45) Date of Patent: Jul. 25, 2017

(54) LIGHT CONDENSING UNIT, LIGHT CONDENSING METHOD, AND OPTICAL DETECTION SYSTEM

(71) Applicant: Sony Corporation, Tokyo (JP)

(72) Inventor: Yoichi Toriumi, Tokyo (JP)

(73) Assignee: Sony Corporation, Tokyo (JP)

( * ) Notice: Subject to any disclaimer, the term of this patent is extended or adjusted under 35 U.S.C. 154(b) by 175 days.

(21) Appl. No.: 14/436,118

(22) PCT Filed: Sep. 13, 2013

(86) PCT No.: PCT/JP2013/074920
§ 371 (c)(1),
(2) Date: Apr. 16, 2015

(87) PCT Pub. No.: WO2014/065039
PCT Pub. Date: May 1, 2014

(65) Prior Publication Data
US 2015/0260579 A1   Sep. 17, 2015

(30) Foreign Application Priority Data

Oct. 26, 2012  (JP) ................................. 2012-236464

(51) Int. Cl.
G02B 19/00       (2006.01)
G01J 3/50        (2006.01)
(Continued)

(52) U.S. Cl.
CPC ................ *G01J 3/50* (2013.01); *G01J 3/021* (2013.01); *G01J 3/0205* (2013.01);
(Continued)

(58) Field of Classification Search
None
See application file for complete search history.

(56) References Cited

U.S. PATENT DOCUMENTS 7,119,897 B2 * 10/2006 Vaez-Iravani .......... G01N 21/47
                                                 356/237.4
7,184,138 B1 *  2/2007 Li ...................... G01N 21/9501
                                                 356/237.2
(Continued)

FOREIGN PATENT DOCUMENTS

JP       62-029506 A     2/1987
JP       63-500263 A     1/1988
(Continued)

*Primary Examiner* — Derek S Chapel
(74) *Attorney, Agent, or Firm* — Wolf, Greenfield & Sacks, P.C.

(57) ABSTRACT

Provided is a light condensing unit including a reflection member having a hollow dome shape a side wall of which is curved to be extended from a top portion toward a bottom portion, the reflection member having a mirror-finished inner surface, and a plurality of light irradiation members arranged around an outer wall of the reflection member and configured to irradiate an irradiation region of the top portion with light through a first opening portion formed in the outer wall. The reflection member includes a second opening portion formed in the irradiation region of the top portion, and a third opening portion formed in the bottom portion to face a light receiving lens of a light receiving unit, the light receiving unit being configured to perform a predetermined process on received light.

28 Claims, 15 Drawing Sheets

(51) Int. Cl.
*G01N 21/25* (2006.01)
*G01J 3/02* (2006.01)
*G01J 3/51* (2006.01)

(52) U.S. Cl.
CPC ........... *G01J 3/0208* (2013.01); *G01J 3/0216* (2013.01); *G01J 3/0256* (2013.01); *G01J 3/513* (2013.01); *G01N 21/255* (2013.01); *G02B 19/0023* (2013.01); *G02B 19/0028* (2013.01); *G02B 19/0047* (2013.01); *G02B 19/0061* (2013.01); *G02B 19/0085* (2013.01)

(56) References Cited

U.S. PATENT DOCUMENTS

| | | | | |
|---|---|---|---|---|
| 7,304,310 | B1 * | 12/2007 | Shortt | G01N 21/94 250/372 |
| 7,477,371 | B2 * | 1/2009 | Marxer | G01N 21/94 356/237.1 |
| 8,289,509 | B2 * | 10/2012 | Wenz | G01N 21/4738 356/237.5 |
| 2009/0159803 | A1 * | 6/2009 | Berthold | G01J 3/02 250/363.01 |
| 2009/0270702 | A1 * | 10/2009 | Zeng | A61B 5/0075 600/323 |
| 2010/0079754 | A1 * | 4/2010 | Kuo | G01J 3/02 356/301 |
| 2010/0252721 | A1 * | 10/2010 | Xu | A61B 5/14532 250/226 |
| 2013/0037720 | A1 * | 2/2013 | Reinke | G01N 21/55 250/341.1 |

FOREIGN PATENT DOCUMENTS

| | | |
|---|---|---|
| JP | 07-167779 A | 7/1995 |
| JP | 10-019779 A | 1/1998 |
| JP | 10-073534 A | 3/1998 |
| JP | 11-083627 A | 3/1999 |
| JP | 2008-518229 A | 5/2008 |
| JP | 2009-145180 A | 7/2009 |
| JP | 2012-032240 A | 2/2012 |
| WO | WO 86/06834 A1 | 11/1986 |
| WO | WO 2006/046913 A1 | 5/2006 |

* cited by examiner

LIGHT CONDENSING UNIT, LIGHT CONDENSING METHOD, AND OPTICAL DETECTION SYSTEM

TECHNICAL FIELD

The present invention relates to a light condensing unit, a light condensation method, and an optical detection system.

BACKGROUND ART

To measure various characteristics of a measurement target object, methods of irradiating the measurement target object with light and detecting reflected light by an imaging device are commonly used.

For example, Patent Literature 1 discloses a coloration substance quantitative determination device that performs a quantitative determination of a coloration substance contained during the solid phase by detecting reflected light from the solid phase. Patent Literature 2 discloses a color reader that reads a color image of an original by irradiating the original with light and detecting reflected light. Patent Literature 3 discloses a system that captures multi-spectral or hyper-spectral images and is capable of scanning a two-dimensional image (multi-spectral image or hyper-spectral image) having more than three bandwidths.

On the other hand, an image sensor generally outputs an electrical signal (pixel signal) depending on the amount of incident light. To obtain a desired output that is sufficient to perform a measurement or image capturing, the corresponding amount of light is necessary to be incident on the image sensor. If an efficient incidence of light from a light source on an image sensor is possible, even when the amount of irradiation from the light source is relatively small, the measurement or image capturing can be implemented with higher sensitivity.

For example, Patent Literature 4 discloses an inspection light irradiation device that includes a cylindrical light condenser having a mirror-finished inner surface provided in an optical path along which the irradiation light from a light source is guided to an image sensor, and an inspection device of solid-state image sensor using it.

CITATION LIST

Patent Literature

Patent Literature 1: JP H10-073534A
Patent Literature 1: JP S62-029506A
Patent Literature 1: JP 2007-538856A
Patent Literature 1: JP 2009-145180A

SUMMARY OF INVENTION

Technical Problem

In general, an image sensor is often used as a sensor module in which the image sensor is combined with a light receiving lens for guiding incident light to the image sensor. This is because an optimal size or curvature of the light receiving lens may vary depending on factors such as a size (light receiving area) of the image sensor or a distance between the image sensor and the light receiving lens. Thus, it is also necessary to consider the characteristics of the light receiving lens in the sensor module in order to allow light to be more efficiently incident on an image sensor.

However, the techniques disclosed in Patent Literatures 1 to 3 have not provided any specific means for efficiently condensing light on the image sensor. The light condenser disclosed in Patent Literature 4 has not been made as a design that takes characteristics of a light receiving lens into consideration, and thus sufficient light condensing efficiency may not be achieved.

Thus, in the present disclosure, there is provided a novel and improved light condensing unit, light condensation method, and optical detection system, capable of more efficiently condensing light on a light receiving lens.

Solution to Problem

According to the present disclosure, there is provided a light condensing unit including a reflection member having a hollow dome shape a side wall of which is curved to be extended from a top portion toward a bottom portion, the reflection member having a mirror-finished inner surface, and a plurality of light irradiation members arranged around an outer wall of the reflection member and configured to irradiate an irradiation region of the top portion with light through a first opening portion formed in the outer wall. The reflection member includes a second opening portion formed in the irradiation region of the top portion, and a third opening portion formed in the bottom portion to face a light receiving lens of a light receiving unit, the light receiving unit being configured to perform a predetermined process on received light. The reflection member guides light coming from the irradiation region and being reflected by the inner surface to the light receiving lens.

According to the present disclosure, there is provided a light condensation method including irradiating an irradiation region with light through a first opening portion by a plurality of light irradiation members, the light irradiation members being arranged around an outer wall of a reflection member, the reflection member having a hollow dome shape a side wall of which is curved to be extended from a top portion toward a bottom portion, the reflection member having a mirror-finished inner surface, the first opening portion being formed in the outer wall, the irradiation region being positioned on the top portion, reflecting irradiation light from the irradiation region by the inner surface and guiding the reflected light to a second opening portion formed in the bottom portion of the reflection member, and allowing the guided light to be incident on a light receiving lens of an image sensor module, the image sensor module being configured to output a pixel signal depending on an amount of received light, the light receiving lens being provided to face the second opening portion.

According to the present disclosure, there is provided a light detection system including an image sensor module provided with a light receiving lens and configured to output a pixel signal depending on an amount of received light through the light receiving lens, and a light condensing unit configured to condense light on the light receiving lens. The light condensing unit includes a reflection member having a hollow dome shape a side wall of which is curved to be extended from a top portion toward a bottom portion, the reflection member having a mirror-finished inner surface, and a plurality of light irradiation members arranged around an outer wall of the reflection member and configured to irradiate an irradiation region of the top portion with light through a first opening portion formed in the outer wall. The reflection member includes a second opening portion formed in the irradiation region of the top portion, and a third opening portion formed in the bottom portion to face a light receiving lens of a light receiving unit, the light receiving unit being configured to perform a predetermined process on received light. The reflection member guides light coming from the irradiation region and being reflected by the inner surface to the light receiving lens.

According to the present disclosure, light coming from the irradiation region is reflected by the inner surface of the reflection member and is guided to the light receiving lens of the light receiving unit. Thus, light coming from the irradiation region is condensed on the light receiving lens.

Advantageous Effects of Invention

According to the present disclosure as described above, it is possible to condense light on the light receiving lens in a more efficient way.

DESCRIPTION OF EMBODIMENTS

Figure 1:
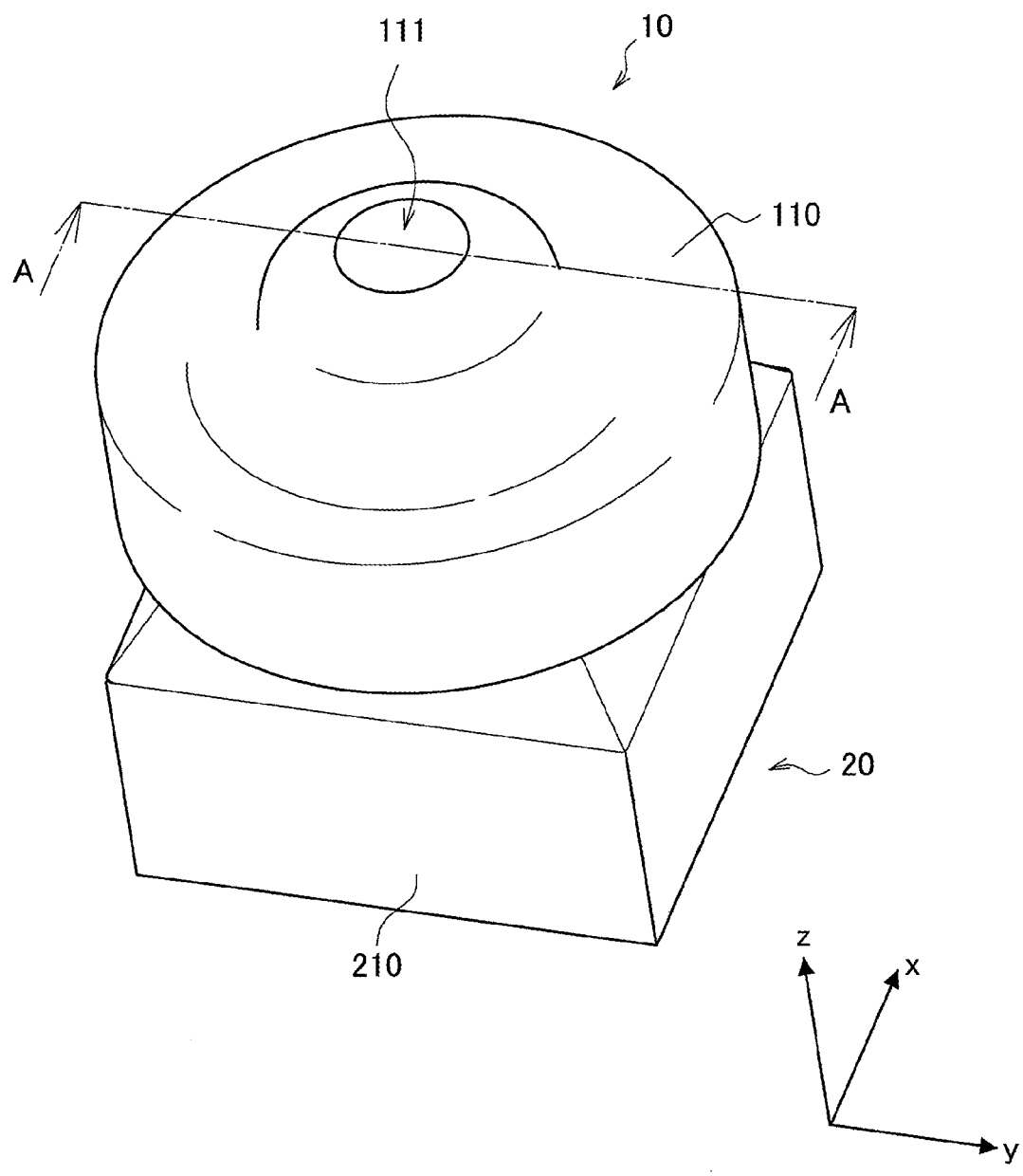
FIG. 1 is a perspective view illustrating how to install a light condensing unit according to a first embodiment of the present disclosure in an image sensor module.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the order below.
1. First Embodiment
1.1. Exemplary appearance of light condensing unit
1.2. Configuration of light condensing unit
1.3. Shape of reflection member
1.4. Light condensing effect
1.5. Application example
2. Second Embodiment
2.1. Configuration of light condensing unit
2.2. Light condensing effect
2.3. Application example
3. Third Embodiment
3.1. Configuration of light condensing unit
3.2. Light condensing effect
4. Modification
4.1. Integration with light receiving lens
4.2. Change in number of light irradiation members
4.3. Other modifications
5. General versatility of reflection member
6. Conclusion A light condensing unit according to the first, second, and third embodiments of the present disclosure is installed in a light receiving unit that performs a predetermined process on received light and has a function of condensing light on the light receiving unit. Here, as a specific example of the light receiving unit, hereinafter, a description will be given by exemplifying an image sensor module. However, the light condensing unit according to the first, second, and third embodiments of the present disclosure is applicable, but not limited to its application of the installation on an image sensor module, to any other types of light receiving units.

<1. First Embodiment>
[1.1. Exemplary Appearance of Light Condensing Unit]
The schematic configuration of the light condensing unit according to the first embodiment of the present disclosure will be first described with reference to FIG. 1. FIG. 1 is a perspective view illustrating how to install the light condensing unit according to the first embodiment of the present disclosure in an image sensor module.

Referring to FIG. 1, the light condensing unit 10 includes a housing 110 having a substantially cylindrical shape. The housing 110 is made of light shielding material and has a space therein that is used to accommodate a reflection member, a light irradiation member, or the like, which will be described later. In addition, in the example shown in FIG. 1, the housing 110 has a projection shape that projects toward the outer direction of the housing 110 substantially at the center of a circular surface on one side of the cylinder.

Note that, in the following description, the direction perpendicular to two circular surfaces that constitute the cylinder of the housing 110 is defined as z-axis. In addition, the direction in which one surface of the housing 110 projects is referred to as upward direction (positive direction of z-axis shown in FIG. 1), and the opposite direction thereof is referred to as downward direction (negative direction of z-axis shown in FIG. 1). In addition, for the light condensing unit 10, two axes perpendicular to each other in the plane parallel to upper and lower surfaces of the housing 110 are defined as x-axis and y-axis.

Referring to FIG. 1, an upper opening portion 111 that communicates the inner space of the housing 110 with the outside is provided in the distal end portion that projects in the positive direction of the z-axis of the housing 110. In addition, although not explicitly shown in FIG. 1, a lower opening portion that communicates the inner space of the housing 110 with the outside is provided substantially at the center of the lower surface (surface positioned in the negative direction of the z-axis) of the housing 110.

In other words, in the housing 110 of the light condensing unit 10, the opening portions are provided at the positions opposite to each other of the upper and lower surfaces of the cylinder. The light, which is applied from the upper opening portion 111 toward the inside of the housing 110, is condensed on the lower opening portion provided in the lower surface of the housing 110 while being guided in the negative direction of the z-axis within the light condensing unit 10, and is emitted from the lower opening portion to the outside.

On the other hand, referring to FIG. 1, an image sensor module 20 is connected to the lower side of the light condensing unit 10. The image sensor module 20 includes a housing 210 having a substantially rectangular parallelepiped shape. The housing 210 is made of light shielding material and has a space therein that is used to accommodate an image sensor or the like. In the following description, two sides perpendicular to each other among four sides that constitute the upper surface and lower surface (bottom surface) of the housing 210 are respectively referred to as x-axis direction and y-axis direction.

In the example shown in FIG. 1, the image sensor module 20 has a projection shape that projects toward the upward substantially at the center of the upper surface of the housing 210. Furthermore, although not explicitly shown in FIG. 1, a light receiving opening portion that allows light to be incident on the inside of the housing 210 is provided in the distal end portion that projects in the positive direction of the z-axis of the housing 210. In the image sensor module 20 according to the present embodiment, the housing 210 may be formed without a projection shape on the upper surface thereof. In this case, the housing 210 has a planar upper surface, and the light receiving opening portion may be provided substantially at the center of the plane.

A light receiving lens is provided in the light receiving opening portion of the image sensor module 20. The light receiving lens guides light that is incident on the housing 210 from the light receiving opening portion to a light receiving surface of the image sensor that is arranged inside the housing 210. In other words, the image sensor module 20 receives the light incident from the light receiving lens of the light receiving opening portion provided on the upper surface of the housing 210 through the image sensor. The image sensor then outputs an electrical signal (pixel signal) depending on the amount of received light.

In the present embodiment, the light condensing unit 10 and the image sensor module 20 are connected in a manner that the lower opening portion provided on the lower surface of the housing 110 faces the light receiving opening portion provided on the upper surface of the housing 210. The light condensing unit 10 has a function of allowing the light, which is applied from the upper opening portion 111 toward the inside of the housing 110, to be condensed on the light receiving lens of the image sensor module 20.

As a specific way of using the light condensing unit 10, a measurement target object is first placed on the upper surface of the upper opening portion 111. Then, light is applied from a light irradiation member provided in the housing 110, which will be described later, toward the upper opening portion 111, that is, to a measurement target object that is placed on the upper opening portion 111. The light reflected from the surface of the measurement target object or light scattered inside the measurement target object is condensed on the lower opening portion provided on the lower surface of the housing 110 and the light receiving lens of the image sensor module 20 connected to the lower opening portion while being guided to the negative direction of the z-axis inside the light condensing unit 10. Thus, it is possible for the light reflected from the surface of the measurement target object or light scattered inside the measurement target object to be efficiently incident on the image sensor provided in the image sensor module 20. Note that, in the following description, the light reflected from the surface of the measurement target object or light scattered inside the measurement target object is called scattered or reflected light.

The function and configuration of the light condensing unit 10 described above will be described below in more detail with reference to FIGS. 2 and 3. Note that, in the following, the description will be given by defining a central axis that indicates the center of the light condensing unit 10 and the image sensor module 20. Specifically, as shown by the dashed line in FIG. 2, an axis that passes through the center of the upper and lower surfaces of the housing 110 of the light condensing unit 10 and the center of the upper and lower surfaces of the housing 210 of the image sensor module 20 in the perpendicular direction to these surfaces is defined as a central axis c.

The light condensing unit 10 and the image sensor module 20 have a symmetrical structure to rotation about the central axis c. For example, in the present embodiment as shown in FIG. 1, the light condensing unit 10 and the image sensor module 20 have a structure of so-called four-fold symmetry to the central axis c. Thus, in the following, in view of the above symmetry, the configuration of the light condensing unit 10 and the image sensor module 20 will be described by mainly using a sectional view taken along section A-A (a section passing through the central axis c in a plane including y-axis and z-axis) shown in FIG. 1.

[1.2. Configuration of Light Condensing Unit]

Next, the configuration of the light condensing unit according to the first embodiment will be described in detail with reference to FIGS. 2 and 3. FIG. 2 is a sectional view of the light condensing unit according to the first embodiment, taken along section A-A of FIG. 1. FIG. 3 is an explanatory diagram illustrated to describe a positional relationship between a reflection member and a light irradiation member in the light condensing unit according to the first embodiment. Note that the function and configuration of the light condensing unit and the image sensor module described above with reference to FIG. 1 may be omitted in the following description.

Figure 2:
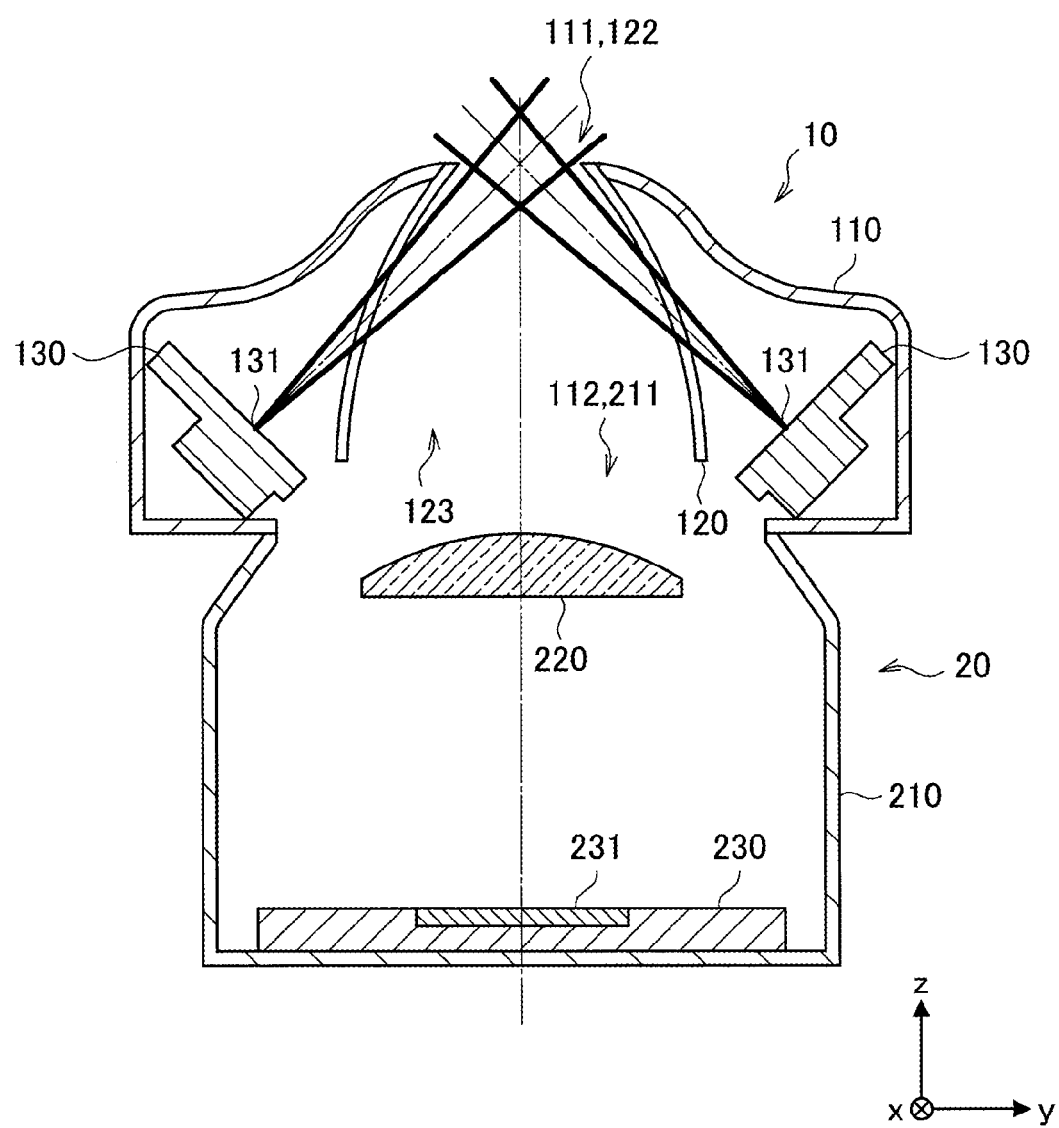
FIG. 2 is a sectional view of the light condensing unit according to the first embodiment, taken along section A-A of FIG. 1.

Referring to FIG. 2, the light condensing unit 10 includes a housing 110, a dome shaped reflection member 120, and a plurality of light irradiation members 130.

The housing 110, for example, as described above with reference to FIG. 1, has a substantially cylindrical shape, and a substantially central portion of the housing 110 projects toward the outside, that is, the upper side shown in FIG. 2.

Furthermore, the housing 110 has a substantially circular upper opening portion 111 in a distal end of the projecting portion, that is, a partial region of the substantially central portion on the upper surface. A substantially circular lower opening portion 112 is provided in a partial region of the substantially central portion on the bottom surface of the housing 110. The upper opening portion 111 and the lower opening portion 112 are provided in a manner that the substantially central portions of the opening portions fall in line with the central axis c of the light condensing unit 10. As a specific dimension of the upper opening portion 111 and the lower opening portion 112, the upper opening portion 111 may have a diameter of approximately 5 millimeters, and the lower opening portion 112 may have a diameter of approximately 10 millimeters, as an example.

The housing 110 has an inner space in which the reflection member 120 and the plurality of light irradiation members 130 are arranged.

The reflection member 120 has a hollow dome shape that is curved in a manner that its side wall is extended from the top portion toward the bottom portion. The reflection member 120 has a mirror-finished inner surface and can reflect light incident on the inner surface.

The reflection member 120 is arranged in the housing 110 in a manner that the top portion of the reflection member 120 corresponds to the upper opening portion 111 of the housing 110. The reflection member 120 is arranged in a manner that the substantially central portion of the top portion of the reflection member 120 and the substantially central portion of the bottom portion thereof fall in line with the central axis c.

The plurality of light irradiation members 130 are arranged around the outer wall of the reflection member 120. A light irradiation portion 131 is provided in a partial region of the light irradiation member 130. The light irradiation member 130 allows the light irradiation portion 131 to apply light in a predetermined direction. In the present embodiment, the light irradiation member 130 includes a light source for emitting white light and an optical member for adjusting the direction of irradiation such as a collimator or aperture stop, as an example. The light source for emitting white light may be a white light emitting diode (LED), as an example.

The configuration of the reflection member 120 and the light irradiation member 130 and the positional relationship between them will be described in more detail with reference to FIG. 3. FIG. 3 illustrates only the reflection member 120 and the light irradiation member 130 among components of the light condensing unit 10, and illustrates the side view of the reflection member 120 and the top view of the light irradiation member 130 in a manner that the positions of the two members are associated with each other.

Figure 3:
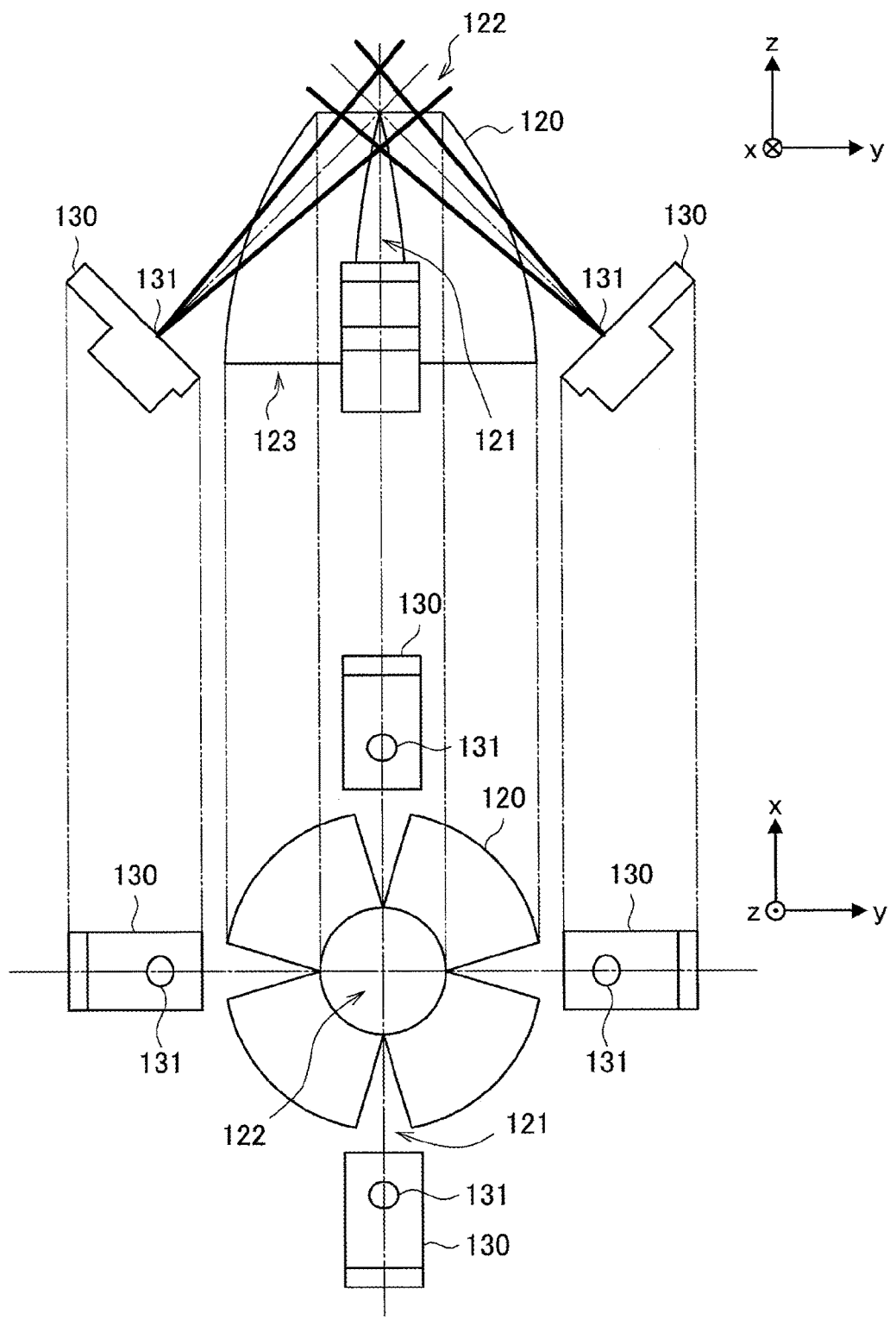
FIG. 3 is an explanatory diagram illustrated to describe a positional relationship between a reflection member and a light irradiation member in the light condensing unit according to the first embodiment.

Referring to FIG. 3, the plurality of light irradiation members 130 are arranged around the outer wall of the reflection member 120, and are disposed in a manner that the light irradiation direction (optical axis) of the light irradiation member 130 faces the top portion of the reflection member 120. A first opening portion 121 is provided in the outer wall of the reflection member 120 at a portion corresponding to an irradiation region of the light irradiation member 130. In other words, the light emitted from the light irradiation member 130 is applied to the vicinity of the top portion of the reflection member 120 through the first opening portion 121 provided in the outer wall of the reflection member 120. In the present embodiment, the first opening portion 121 may be a slit formed in the outer wall of the reflection member 120. In the following description, the region is irradiated with light emitted by the light irradiation member 130 is referred to as irradiation region.

Moreover, a second opening portion 122 having a substantially circular shape is provided in the top portion, that is, the irradiation region, of the reflection member 120. The bottom surface of the reflection member 120 is opened over the entire region and constitutes a third opening portion 123 having a substantially circular shape. As a specific dimension of the second opening portion 122 and the third opening portion 123, the second opening portion 122 may have a diameter of approximately 5 millimeters, and the third opening portion 123 may have a diameter of approximately 10 millimeters, as an example.

As a specific way of using the light condensing unit 10 as described above, for example, a measurement target object is placed on the upper surface of the upper opening portion 111. Then, the measurement target object placed on the upper surface of the upper opening portion 111 is irradiated with light that passes through the first opening portion 121, the second opening portion 122, and the upper opening portion 111 from the plurality of light irradiation members 130. Thus, the irradiation region may be a concept that indicates the entire region irradiated with light in the measurement target object, the second opening portion 122, and the upper opening portion 111.

Referring to FIG. 3, the plurality of light irradiation members 130 are arranged at substantially equal intervals around the outer wall of the reflection member 120. In the present embodiment, the light condensing unit 10 includes four light irradiation members 130, as an example. Thus, the light irradiation members 130 are arranged at intervals of 90 degrees around the outer wall of the reflection member 120.

The plurality of light irradiation members 130 are arranged in a manner that the optical axes of the light irradiation members 130 are intersected with each other at a substantially central portion of the irradiation region. More specifically, the plurality of light irradiation members 130 may be arranged in a manner that the optical axes of the light irradiation members 130 are intersected with each other substantially at the surface of the measurement target object that is placed on the upper surface of the upper opening portion 111. This arrangement of the light irradiation member 130 allows the irradiation region to be irradiated with light having a uniform angle of incidence from each direction.

The irradiation region, for example, a measurement target object may be irradiated at an angle of incidence of 45 degrees with light emitted from the light irradiation member 130. The irradiation region, for example, a measurement target object may be irradiated, for example, at a numerical aperture (NA) of 0.2 with light emitted from the light irradiation member 130. The distance between the measurement target object and the center point (emission center point) of the light irradiation portion 131 of the light irradiation member 130 may be 12.6 millimeters, as an example.

Referring back to FIG. 2, the description will be continuously given of the configuration of the light condensing unit 10 and the image sensor module 20. The image sensor module 20 includes the housing 210, a light receiving lens 220, and an image sensor 230.

The housing 210 has a substantially rectangular parallelepiped shape, and has an upper surface with a substantially central portion that projects upward, as an example. The housing 210 has a light receiving portion 211 in a distal end of the projecting portion, that is, a partial region of the substantially central portion on the upper surface. The light receiving opening portion 211 is provided in a manner that the substantially central portion of the light receiving opening portion 211 falls in line with the central axis c. In the image sensor module 20 according to the present embodiment, the housing 210 may be formed without a projection shape on the upper surface thereof. In this case, the housing 210 has a planar upper surface, and the light receiving opening portion 211 may be provided substantially at the center of the plane.

The light receiving lens 220 is provided in the light receiving opening portion 211. The light receiving lens 220 has a function of guiding the received light to a light receiving surface of the image sensor 230 arranged in the housing 210. The light receiving lens 220 is arranged in a manner that a substantially central portion of the light receiving lens 220 falls in line with the central axis c.

The light receiving lens 220 has optimized curvature and refractive index to efficiently guide the light incident on the light receiving lens 220 to the light receiving surface 231 of the image sensor 230. For example, the light receiving lens 220 has optimized curvature and refractive index so that the light that is incident from the middle to the far end (for example, approximately 20 to 30 centimeters) is efficiently guided to the light receiving surface of the image sensor 230 and then an image is formed on the light receiving surface. For example, the light receiving lens 220 is a spherical lens having a diameter (lens diameter) of 10 millimeters, a curvature of 0.1, and a refractive index of 1.8 to 1.9 for visible light. The light receiving lens 220 may have a converging angle of 29 degrees. When a measurement target object is placed on the upper surface of the upper opening portion 111, the distance between the measurement target object and the light receiving lens 220 may be 11.5 millimeters, as an example.

In the housing 210, the image sensor 230 is placed substantially at the center of the bottom surface of the housing 210. The image sensor 230 has the light receiving surface 231 formed on one surface of the image sensor 230, and outputs an electrical signal (pixel signal) depending on the amount of light incident on the light receiving surface 231. The outputted pixel signal is transmitted to an external information processing device or the like of the image sensor via a cable (not shown) or other connection. The information processing device performs appropriate signal processing on the pixel signal, thereby acquiring various data such as image data or an optical spectrum.

The image sensor 230 is arranged on the bottom surface of the housing 210 in a manner that the light receiving surface 231 faces upward (positive direction of z-axis). The image sensor 230 is arranged in a manner that a substantially central portion of the light receiving surface 231 falls in line with the central axis c. The image sensor 230 may be a solid-state image sensor such as a CCD sensor or CMOS sensor, as an example. The light receiving surface 231 may be configured to include a two-dimensional array of light receiving elements such as a photodiode (PD), as an example. The light receiving surface 231 may have a size of 8.8 (x-axis direction)×6.6 (y-axis direction) millimeters, as an example.

As shown in FIG. 2, the light condensing unit 10 is connected to the image sensor module 20 in a manner that the lower opening portion 112 of the light condensing unit 10 and the third opening portion 123 of the reflection member 120 face a light receiving opening portion 211 (light receiving lens 220) of the image sensor module 20. The lower opening portion 112 of the housing 110 has substantially the same area as the light receiving opening portion 211 of the housing 210. When the light condensing unit 10 and the image sensor module 20 are connected to each other, the lower opening portion 112 and the light receiving opening portion 211 are designed in a manner as to fit the housing 110 and the housing 210 with no gap between them to prevent the entry of light from the outside. When the light condensing unit 10 and the image sensor module 20 are connected to each other in a manner that the substantially central portions of the upper opening portion 111, the second opening portion 122, the third opening portion 123, the light receiving opening portion 211, the light receiving lens 220, and the light receiving surface 231 all pass through the central axis c.

The reflection member 120, the light irradiation member 130, and the light receiving lens 220 are fixed to the inner walls of the housing 110 and the housing 210 by a support member or the like, and thus the relative position between these three components is fixed. However, the material of the support member or the way to fix the reflection member 120, the light irradiation member 130, and the light receiving lens 220 is not particularly limited, but any material or way may be employed as long as the relative position between the reflection member 120, the light irradiation member 130, and the light receiving lens 220 is fixed. In FIGS. 2 and 3, and the figures described later, illustration of the support member is omitted for the sake of simplicity of illustration.

The configuration of the light condensing unit 10 according to the first embodiment has been described with reference to FIGS. 2 and 3. In addition, as an example of the light receiving unit equipped with the light condensing unit 10, the configuration of the image sensor module 20 has been described.

With the configuration described above, the light applied to the inside of the light condensing unit 10 from the upper opening portion 111 is reflected from the inner wall of the reflection member 120, and the reflected light is condensed to be incident on the light receiving lens 220 provided in the light receiving opening portion 211, and then the light is guided to the image sensor 230. Thus, the use of the light condensing unit 10 makes it possible for the light to be incident on the image sensor 230 in a more efficient manner.

As an example of the specific way of using the light condensing unit 10, as described above with reference to FIG. 1, a measurement target object is placed on the upper opening portion 111 of the light condensing unit 10 so as to close the upper opening portion 111 from the outside of the housing 110 (from the positive direction of z-axis). A portion of the measurement target object that is in contact with the upper opening portion is irradiated with light emitted from the plurality of light irradiation members 130. The light applied to the measurement target object is reflected from the surface of the measurement target object or scattered inside the measurement target object, and then comes back to the inside of the housing 110. The scattered or reflected light from the measurement target object, that is, the light applied to the inside of the housing 110 from the irradiation region is reflected from the inner wall of the reflection member 120, passes through the lower opening portion 112, and is condensed on the light receiving lens 220 provided in the light receiving opening portion 211. The light, which is condensed on the light receiving lens 220, is then detected by the image sensor 230. Thus, it is possible to condense the scattered or reflected light and to make the light incident on the image sensor in a more effective manner.

In the above description, although the substantially central portion of the light receiving lens 220 and the substantially central portion of the light receiving surface 231 are positioned to fall in line with the central axis c, the present embodiment is not limited to this example. The substantially central portion of the light receiving lens 220 and the substantially central portion of the light receiving surface 231 may not necessarily be positioned on one straight line. In other words, in the image sensor module 20, one or more optical elements such as lens or mirror may be further provided, and an optical path for guiding the light incident from the light receiving lens 220 to the light receiving surface 231 of the image sensor 230 may be formed. Thus, in the present embodiment, the optical path along which the light condensed on the light receiving lens 220 by the light condensing unit 10 reaches the image sensor 230 within the image sensor module 20 is not particularly limited, the configuration of various optical elements within the image sensor module 20, which is used to form the optical path, may be designed in an appropriate manner.

[1.3. Shape of Reflection Member]

Figure 4:
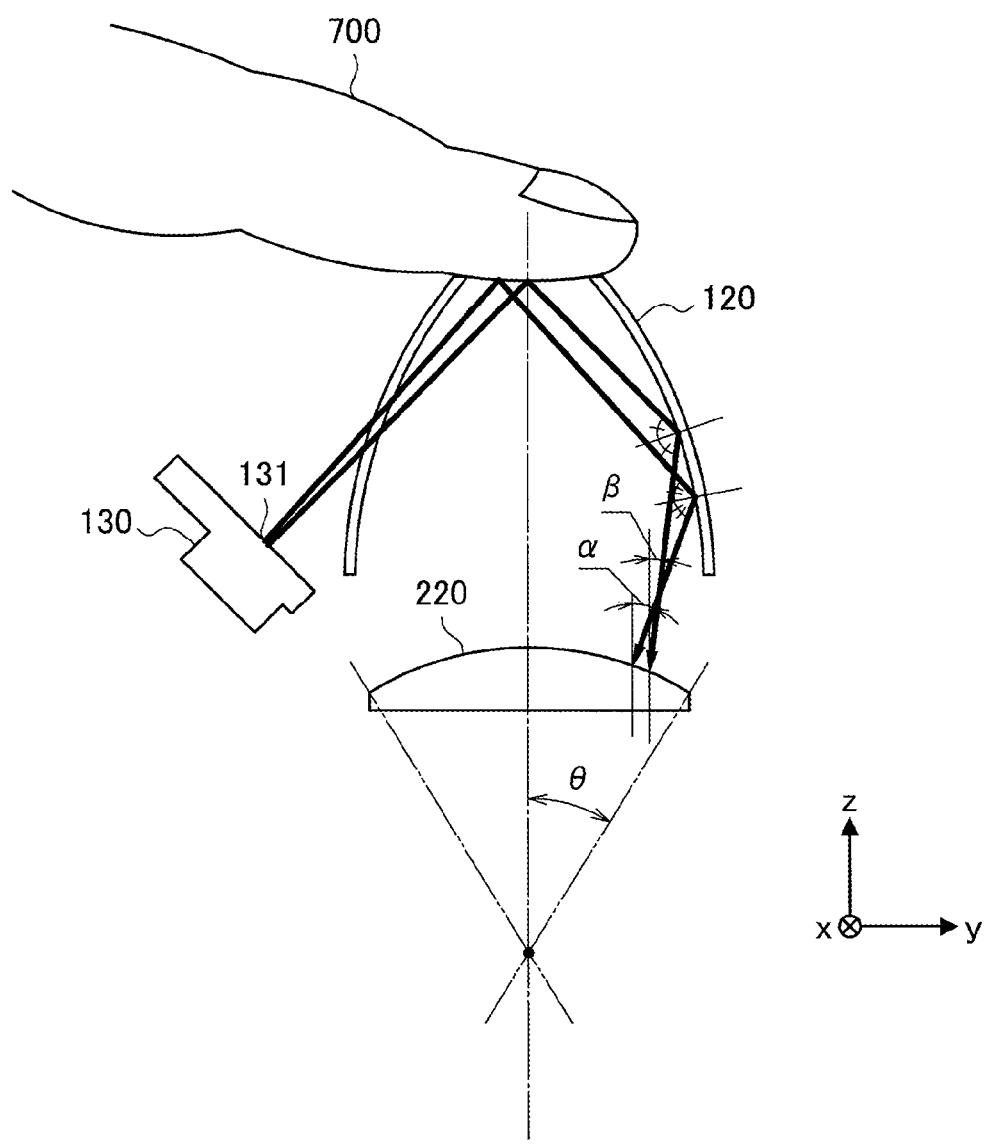
FIG. 4 is an explanatory diagram illustrated to describe the shape of the reflection member.

Next, the shape of the reflection member 120 included in the light condensing unit 10 according to the first embodiment will be described in detail with reference to FIG. 4. FIG. 4 is an explanatory diagram illustrated to describe the shape of the reflection member 120.

FIG. 4 illustrates only the reflection member 120, the light irradiation member 130, and the light receiving lens 220 among components in the sectional view of the light condensing unit 10 and the image sensor module 20 shown in FIG. 2. In FIG. 4, for the sake of simplicity of description, only one of the plurality of light irradiation members 130 is illustrated. The arrow shown in the figure schematically denotes the optical path of the light emitted from the light irradiation member 130. Furthermore, to describe the shape of the reflection member 120, a measurement target object 700, that is, for example, the finger that is a part of the human body is placed on the upper portion of the second opening portion 122 in accordance with the way of using the light condensing unit 10 as described above.

Referring to FIG. 4, the light irradiation member 130 irradiates the measurement target object 700 with light through the first opening portion 121 of the reflection member 20. The light reflected from the surface of the measurement target object 700 is reflected by the inner wall of the reflection member 120 and is incident on the light receiving lens 220. When the measurement target object 700 is a part of a living body, the reflected light from the measurement target object 700 also includes, in practice, the light emitted toward the outside after being scattered multiple times within the measurement target object 700 in addition to the light reflected from the surface of the measurement target object 700. In FIG. 4, for the sake of simplicity of description, illustration of scattering light or the like within the measurement target object 700 is omitted and only reflected light from the surface of the measurement target object 700 is illustrated.

In this exemplary embodiment, the light receiving lens 220 has a predetermined focal length and converging angle θ as the characteristics of the lens. The light receiving lens 220 can condense the light incident at a lower angle of incidence than the converging angle θ on an optical element arranged apart at a predetermined distance, for example, the light receiving surface 231 of the image sensor 230. The focal length and converging angle are determined depending on a curvature of the lens surface of the light receiving lens, refractive index of the material of the lens, or the like. As the characteristics of the lens, the longer the focal length, the narrower the converging angle θ, and the shorter the focal length, the wider the converging angle θ.

In the present embodiment, the shape of the reflection member 120 is designed depending on the converging angle θ of the light receiving lens. Specifically, the shape of the reflection member 120 is designed in a manner that the angles of incidence α and β on the light receiving lens 220 of the light reflected by the inner wall of the reflection member 120 are smaller than the converging angle θ of the light receiving lens 220. Thus, in the present embodiment, the light reflected by the inner surface of the reflection member 120 is incident on the light receiving lens 220 at the angle of incidence that is smaller than the converging angle θ of the light receiving lens 220 and is guided to the light receiving surface 231 of the image sensor 230.

In other words, in the light condensing unit 10 according to the present embodiment, the shape of the reflection member 120 is designed depending on the lens characteristics of the light receiving lens 220 of the light receiving unit 20 equipped with the light condensing unit 10.

As an example of an expected specific configuration of the light condensing unit 10 according to the present embodiment, the configuration described below may be considered. As an example, the configuration in which the light receiving lens 220 has a relatively long focal length and the distance between the measurement target object 700 and the light receiving lens 220 is relatively shorter than the focal length may be expected. As an example, in the configuration described above, the light receiving lens 220 has a specification that forms an image of a subject with light coming from the middle to the far end (for example, approximately 20 to 30 centimeters). On the other hand, the scattered or reflected light from the measurement target object 700 is applied to the light receiving lens 220 from a proximal end (for example, approximately one centimeter) relative to the middle or far end.

With such a configuration, the reflection member 120 according to the present embodiment, the scattered or reflected light from the measurement target object 700 (from the proximal end) is allowed to be incident on the light receiving lens 220 at an angle of incidence that is equal to the image-forming light coming from the middle to the far end. In other words, the shape of the reflection member 120 is designed in a manner that the scattered or reflected light from the measurement target object located in a proximal end is reflected by the inner wall of the reflection member 120 and is incident on the light receiving lens 220 at an angle of incidence that is equal to the image-forming light coming from the middle to the far end.

Thus, the use of the light condensing unit 10 according to the present embodiment makes it possible for the image sensor module 20 that includes the light receiving lens 220 having a relatively long focal length to receive efficiently the light coming from the distance corresponding to the so-called close-up shot. In other words, it is possible for an existing image sensor module 20 to achieve efficient light condensation without any change in the configuration of the image sensor module 20.

The configuration of the light condensing unit 10 according to the first embodiment has been described in detail with reference to FIGS. 1, 2, 3, and 4. As described above, the light condensing unit 10 according to the first embodiment includes the reflection member 120 and the plurality of light irradiation members 130. The reflection member 120 has a dome shape, and the inner surface of the reflection member 120 is a mirror-finished surface. The light irradiation member 130 is arranged around the reflection member 120. The light emitted from the light irradiation member 130 is applied to the irradiation region of the top portion of the reflection member 120 through the first opening portion 121 provided in the side wall of the reflection member 120. The measurement target object is arranged in contact with the irradiation region, for example, the upper portion of the second opening portion 122, and the light emitted from the light irradiation member 130 is reflected from the surface of the measurement target object or is scattered within the measurement target object. The scattered or reflected light from the measurement target object is reflected by the inner surface of the reflection member 120, passes through the third opening portion 123 provided on the bottom surface of the reflection member 120, and is incident on the light receiving lens 220 of the light receiving unit, for example, the image sensor module 20 provided to face the third opening portion 123.

In this case, the shape of the reflection member 120 is designed depending on the converging angle of the light receiving lens 220. Specifically, the shape of the reflection member 120 is designed in a manner that the angle of incidence on the light receiving lens 220 of the light reflected by the inner surface of the reflection member 120 is smaller than the converging angle of the light receiving lens 220. Thus, the scattered or reflected light from the measurement target object can be incident on the light receiving lens 220 at an angle of incidence that is smaller than the converging angle of the light receiving lens 220 by allowing the scattered or reflected light to be reflected by the inner surface of the reflection member 120, thereby achieving the improved light condensing efficiency.

In this way, in the light condensing unit 10 according to the first embodiment, the shape of the reflection member 120 is designed depending on the converging angle of the light receiving lens 220. Thus, the reflection member 120 can condense the light on the light receiving lens 220 to be suitable for the optical characteristics of the light receiving lens 220, and thus it is possible to improve the light condensing efficiency.

Furthermore, in the light condensing unit 10 according to the first embodiment, the reflection member 120 may have a shape designed in a manner that the scattered or reflected light from the measurement target object located in a proximal end is incident on the light receiving lens 220 at an angle of incidence that is equal to the image-forming light coming from the middle to the far end by reflecting the scattered or reflected light by the inner wall of the reflection member 120. In other words, even when the light receiving lens 220 has a specification that forms an image of a subject with light at a relatively far distance of the middle to the far end (for example, approximately 20 to 30 centimeters) and the scattered or reflected light from the measurement target object is applied to the light receiving lens 220 from a proximal end (for example, approximately 1 centimeter) relative to the middle or far end, the irradiation light coming from the distance corresponding to the so-called close-up shot can be condensed in a more efficient manner.

[1.4. Light Condensing Effect]

The light condensing effect of the light condensing unit 10 according to the first embodiment will be described with reference to FIGS. 5 and 6. The description will be given of the light condensing effect of the light condensing unit 10 based on the results obtained by performing ray-tracing simulation on the light condensing unit 10 according to the first embodiment and the image sensor unit 20 equipped with the light condensing unit 10.

Figure 5:
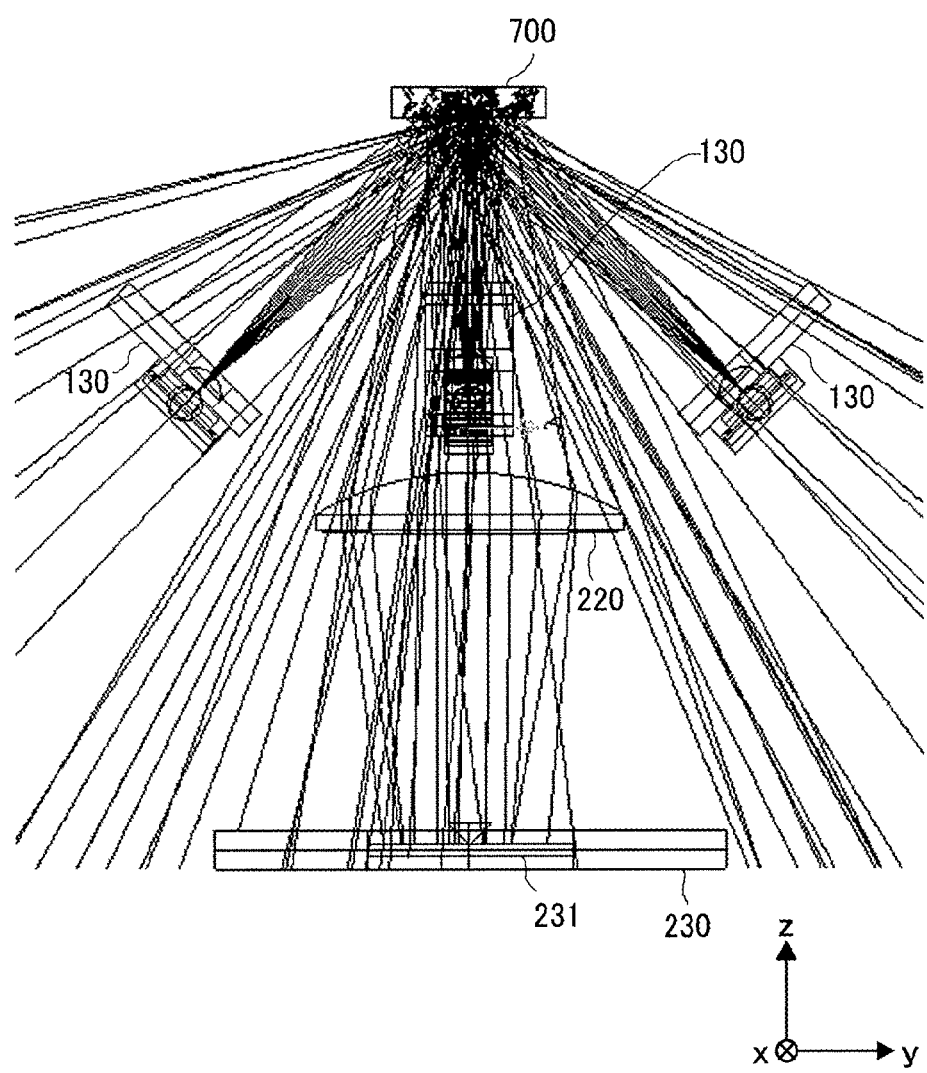
FIG. 5 is a schematic diagram illustrating results of ray-tracing simulation when the light condensing unit according to the first embodiment is not provided with the reflection member.

FIG. 5 is a schematic diagram illustrating results obtained by ray-tracing simulation when the light condensing unit according to the first embodiment is not provided with the reflection member. FIG. 6 is a schematic diagram illustrating results obtained by ray-tracing simulation when the light condensing unit according to the first embodiment is provided with the reflection member.

Figure 6:
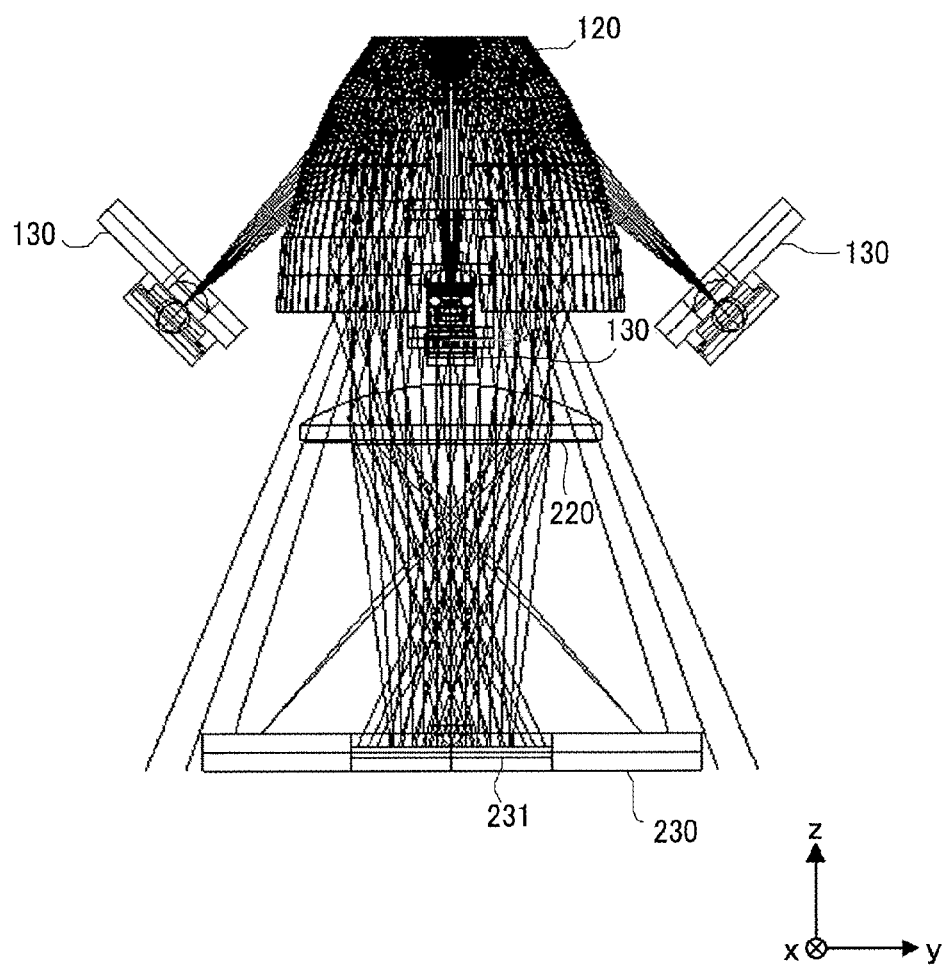
FIG. 6 is a schematic diagram illustrating results of ray-tracing simulation when the light condensing unit according to the first embodiment is provided with the reflection member.

A model of computation in the ray-tracing simulation shown in FIGS. 5 and 6 is prepared based on the light condensing unit 10 and the image sensor module 20 shown in FIG. 2. In FIGS. 5 and 6, for ease of understanding the ray-tracing results, the illustration of other components than the reflection member 120, the light irradiation member 130, the light receiving lens 220, and the image sensor 230 included in the light condensing unit 10 and the image sensor module 20 is omitted. In the model of computation, the measurement target object 700 is placed on the upper portion of the upper opening portion 111. The measurement target object 700 is assumed to be a part of the human body, and a value of physical quantity corresponding to a part of the human body is assigned to the measurement target object 700 to allow the reflection, scattering, or the like of the light in the human body to be represented. In the model of computation, so as to more accurately simulate the reflection of light at the inner surface of the reflection member 120, the side wall of the reflection member 120 is divided into a plurality of grids, and thus the shape of the curved surface of the side wall is represented.

In the model of computation in the ray-tracing simulation, as an example of the specific configuration of the light condensing unit 10 and the image sensor module 20, the shape of each component or the distance between components is set to represent "the configuration in which light receiving lens 220 has a specification that forms an image of a subject with light coming from the middle to the far end (for example, approximately 20 to 30 centimeters), while the scattered or reflected light from the measurement target object 700 is applied to the light receiving lens 220 from a proximal end (for example, approximately one centimeter) relative to the middle or far end" described in the item [1.3. Shape of reflection member] described above.

FIG. 5 shows results obtained by performing the ray-tracing simulation when the reflection member 120 is not provided in the light condensing unit 10 according to the first embodiment. Referring to FIG. 5, we found that the scattered or reflected light from the measurement target object 700 is hardly incident on the light receiving lens 220. Even the light that is incident on the light receiving lens 220, the angle of incidence of the light is excessively large, and thus we found that some of the light is incident on the light receiving surface 231 of the image sensor 230.

FIG. 6 shows results obtained by performing the ray-tracing simulation when the reflection member 120 is provided in the light condensing unit 10 according to the first embodiment. In FIG. 6, the shape of the reflection member 120 may be designed in a manner that the angle of incidence on the light receiving lens 220 of the light reflected by the inner surface of the reflection member 120 is smaller than the converging angle of the light receiving lens 220.

Referring to FIG. 6, we found that the scattered or reflected light from the measurement target object is reflected by the inner surface of the reflection member 120 and most of the reflected light is condensed on the light receiving lens 220. In addition, we found that most of the light incident on the light receiving lens 220 is incident on the light receiving surface 231 of the image sensor 230. This is because the shape of the reflection member 120 is formed depending on the converging angle of the light receiving lens 220, as described in the above item [1.3. Shape of reflection member].

In the ray-tracing simulation shown in FIGS. 5 and 6, we found that the incidence efficiency is improved by nearly three times by providing the reflection member 120 from the result of the computation of incidence efficiency of the light on the light receiving surface 231 of the image sensor 230. It is apparent from the results that the light condensing effect of the light condensing unit 10 according to the first embodiment can be achieved.

As described above with reference to FIGS. 5 and 6, the use of the light condensing unit 10 according to the present embodiment makes it possible to further improve the light condensing efficiency on the light receiving unit connected to the light condensing unit 10. Thus, it is possible to improve the incidence efficiency on the light receiving surface 231 of the light receiving unit, for example, the image sensor module 20. Consequently, for example, the S/N ratio of the pixel signal obtained by the image sensor 230 is improved, and the detection of light is implemented with higher sensitivity.

[1.5. Application Example]

A specific application example of the light condensing unit 10 according to the first embodiment will be described. As an application example of the light condensing unit 10 according to the first embodiment, for example, it is considered that a part (skin) of the human body is used as the measurement target object 700 and the image sensor module 20 measures the optical spectrum of the scattered or reflected light.

For example, R (red), G (green), and B (blue) color filters are provided in each of light receiving elements (pixels) constituting the light receiving surface 231 of the image sensor 230, and the image sensor 230 can spectrally disperse the incident light. In other words, the image sensor 230 can spectrally disperse the scattered or reflected light from the measurement target object 700 into three bands R, G, and B. Three values of R, G, and B dispersed for each pixel are integrated in units of vertical synchronization signal $V_{sync}$ of the image sensor 230, and thus three spectral values for one frame screen of the measurement target object 700 are obtained.

The integration for obtaining three spectral values is performed in units of N times (integral multiplication) of $V_{sync}$, and three spectral values of R, G, and B of the sum or average for N frame screens of the measurement target object 700 may be obtained. While the scattered or reflected light from the measurement target object 700 is incident on the image sensor 230, the integration for obtaining three spectral values is performed intermittently every frame or every N frames, and thus variation with time of three spectral values of the measurement target object 700 may be measured. The various signal processing to calculate three spectral values of R, G, and B from a pixel signal may employ any known signal processing technique commonly used in the field of signal processing related to the image sensor.

From the three spectral values obtained in this way, it is possible to estimate the concentration of a substance contained in the measurement target object 700 by using the Lambert-Beer's law or the like. For example, in the present application example, the measurement target object 700 is a part of the human body, and the spectral curve of the human skin is known to be highly dependent on the amount of melanin pigment in the epidermis and the concentration of hemoglobin in the red blood cells. Thus, if the three spectral values obtained by the scattered or reflected light from a part of the human body that is the measurement target object 700 can be associated with the spectral curve, it is possible to estimate the amount of melanin pigment in the epidermis and the concentration of hemoglobin in the red blood cells in the part of the human body from the associated relationship.

Figure 7:
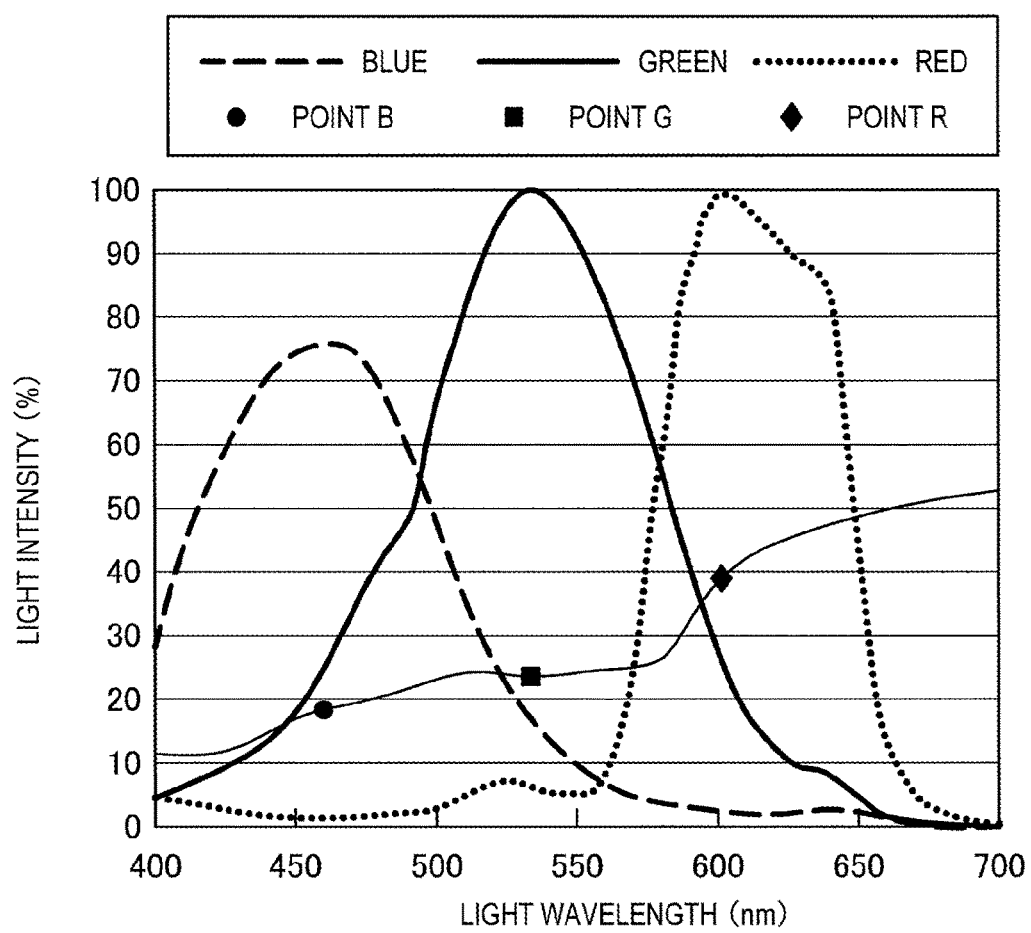
FIG. 7 is a spectral diagram illustrating an optical spectrum detected by the image sensor module equipped with the light condensing unit according to the first embodiment of the present disclosure.

FIG. 7 illustrates the optical spectrum of the scattered or reflected light in the human skin, which is obtained by the image sensor module 20 by using the light condensing unit 10. FIG. 7 is a spectral diagram illustrating an optical spectrum detected by the image sensor module 20 equipped with the light condensing unit 10 according to the first embodiment.

In FIG. 7, the spectral reflectance curve of the human skin is represented by a thin solid line, spectral characteristics of a red (R) color filter are represented by a dotted line, spectral characteristics of a green (G) color filter are represented by a thick solid line, and spectral characteristics of a blue (B) color filter are represented by a broken line. The three spectral values of R, G, and B of the scattered or reflected light in the human skin, which is obtained by the image sensor module 20 using the light condensing unit 10, are respectively plotted as points R, G, and B.

Referring to FIG. 7, three spectral values of R, G, and B shown at point R, point G, and point B are well corresponded to the spectral reflectance curve (thin solid line) of the human skin. In other words, it is possible to obtain data corresponding to the spectral reflectance curve of the human skin from the three spectral values of R, G, and B that are optical spectra of the scattered or reflected light in the human skin, which are obtained by the image sensor module 20 equipped with the light condensing unit 10. Thus, the amount of melanin pigment or the concentration of hemoglobin can be estimated from the three spectral values.

The process of calculating three spectral values of R, G, and B based on the pixel signal outputted from the image sensor 230 and the process of estimating the amount of melanin pigment or the concentration of hemoglobin based on three spectral values of R, G, and B may be performed by any information processing device provided outside of the image sensor module 20. In other words, the pixel signal outputted from the image sensor 230 is transmitted to any information processing device by any communication means, for example, via wired or wireless communication, and the information processing device may perform various data processing.

Moreover, it is possible to estimate a mental condition of a subject such as a case of being excited condition or being relaxed, from the estimated value of the melanin pigment or concentration of hemoglobin. Thus, for example, when a viewer views various kinds of video content or when a user plays a video game, it is possible to recognize in real time which scene in the content leads the viewer or user to a state of excitement or relaxation by measuring the optical spectrum of the human skin. Hence, for example, a change in the contents of game or video content can provide a viewing and operation experience with a sense of presence for the viewer or user depending on the transition to the state of excitement or relaxation.

In recent years, a camera function has been installed in various portable devices such as mobile phones as a standard specification. For example, the image sensor module used in the camera function of a mobile phone has a focal length of approximately 20 to 30 centimeters. Thus, this image sensor module may be an image sensor module equipped with a light receiving lens having a specification that forms an image of a subject with light coming from the middle to the far end, as described above.

The light condensing unit 10 according to the first embodiment can preferably condense the light on the image sensor module equipped with the light receiving lens having a specification that forms an image of a subject with light at a relatively far distance of the middle to the far end, as described above. Thus, as a more preferred application example of the light condensing unit 10, it is conceivable to use the light condensing unit 10, for example, when video content is viewed or a game is played using a mobile phone.

For example, a case where a user plays various kinds of game content using the mobile phone is considered. In this case, the above-described three spectral values of R, G, and B that are optical spectra of the scattered or reflected light in the human skin are calculated, and software used to estimate the melanin pigment or concentration of hemoglobin is previously stored in the mobile phone. The user installs the light condensing unit 10 in a portion where a lens for shooting of the mobile phone is provided and plays various kinds of game content on the mobile phone while the finger is in contact with the upper opening portion 111 of the light condensing unit 10. Then, it is observed in real time that the viewer is in excited condition while playing the game content, and thus the contents of the game content is controlled, for example, the development of the story is changed depending on the excited condition. Thus, it is possible to provide content full of sense of presence for the user depending on the mental condition of the user.

The application example of the light condensing unit 10 according to the first embodiment has been described in detail. In the above, as the specific application example of the light condensing unit 10, the process of estimating the amount of melanin pigment or concentration of hemoglobin from the optical spectra of the human skin, which are obtained by the image sensor unit 20 equipped with the light condensing unit 10, has been described. However, the application example of the light condensing unit 10 according to the first embodiment is not limited thereto, and various kinds of biometric information, which relates to a human being and can be estimated from the optical spectra of the human skin, may be obtained.

In the above, although there has been described the case where the light condensing unit 10 is installed in the camera portion of the mobile phone as the specific application example of the light condensing unit 10, the application example of the light condensing unit 10 according to the present embodiment is not limited thereto. For example, the use of installing the light condensing unit 10 in the camera portion of a display device, PC, or the like with a videophone function and displaying various kinds of content on its display screen may be considered. Furthermore, for example, a separate camera module is prepared and equipped with the light condensing unit 10, and then the camera module may be connected to any display device.

<2. Second Embodiment>

The schematic configuration of the light condensing unit according to a second embodiment of the present disclosure will be described. The light condensing unit according to the second embodiment of the present disclosure has substantially the same configuration as the light condensing unit according to the first embodiment described above, except that the light condensing unit according to the second embodiment includes a collimating lens, which will be described later. Thus, in the following description of the light condensing unit according to the second embodiment, description of the configuration that is the same as the light condensing unit according to the first embodiment will be omitted, and the configuration that is different from the light condensing unit according to the first embodiment will be mainly described.

[2.1. Configuration of Light Condensing Unit]

The schematic configuration of the light condensing unit according to the second embodiment of the present disclosure will be first described with reference to FIG. 8. The light condensing unit according to the second embodiment is similar in appearance to the light condensing unit according to the first embodiment shown in FIG. 1, and thus description thereof will be omitted.

Figure 8:
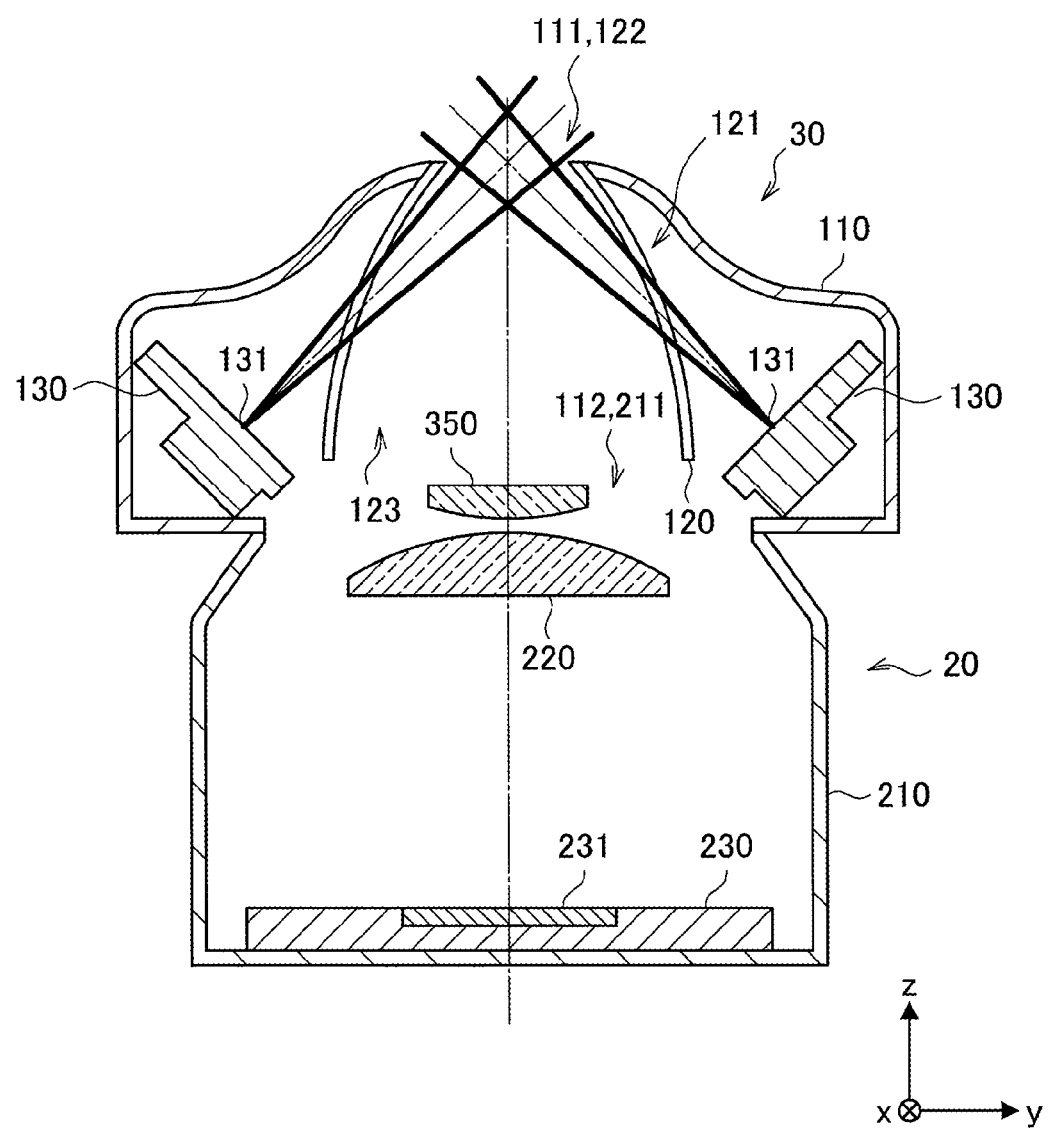
FIG. 8 is a sectional view of a light condensing unit according to a second embodiment of the present disclosure, taken along section A-A in FIG. 1.

FIG. 8 is a sectional view of the light condensing unit according to the second embodiment of the present disclosure, taken along section A-A in FIG. 1. Referring to FIG. 8, the light condensing unit 30 according to the second embodiment further includes a collimating lens 350 disposed between the reflection member 120 and the lower opening portion 112. In other words, the light condensing unit 30 according to the second embodiment further includes the collimating lens 350 at a position that faces the light receiving lens 220 of the image sensor module 20.

The collimating lens 350 constitutes a collimator by making a pair with the light receiving lens 220. The collimating lens 350 has a function of correcting a portion of the scattered or reflected light from the measurement target object (irradiation light from the irradiation region) to produce parallel light.

For example, the collimating lens 350 is a spherical lens and is arranged in a manner that the center of the collimating lens 350 is positioned on the central axis c. The collimating lens 350 is arranged at a position spaced apart from the light receiving lens 220 by a predetermined distance. The separation distance between the collimating lens 350 and the light receiving lens 220 may be 0.5 millimeters, as an example.

The collimating lens 350 may have a diameter (lens diameter) that is nearly half of the lens diameter of the light receiving lens 220. The collimating lens 350 may have a lens diameter of 5 millimeters, as an example.

The surface of the collimating lens 350 that faces the light receiving lens 220 may have a curvature that is substantially the same as the curvature of the light receiving lens 220. The curvature of the surface of the collimating lens 350 that faces the light receiving lens 220 may be 0.1, as an example.

The collimating lens 350 may have a refractive index that is substantially the same as the refractive index of the light receiving lens 220. The refractive index of the collimating lens 350 for visible light may be 1.8 to 1.9, as an example.

A measurement target object is placed on the upper portion of the upper opening portion 111 of the light condensing unit 30 according to the second embodiment, which is similar to the light condensing unit 10 according to the first embodiment.

With the configuration described above, in the light condensing unit 30, the collimating lens 350 constitutes a collimator by making a pair with the light receiving lens 220, corrects a portion of the scattered or reflected light from the measurement target object (irradiation light from the irradiation region) to produce parallel light, and allows the parallel light to be incident on the light receiving surface 231 of the image sensor 230. Thus, the light condensing unit 30 including the collimating lens 350 allows a portion of the scattered or reflected light (irradiation light from the irradiation region) to form an image on the light receiving cell surface of the image sensor 230.

Thus, the light condensing unit 30, which further includes the collimating lens 350, has an imaging function of capturing a portion of the surface of the measurement target object in addition to the function of condensing the scattered or reflected light from the measurement target object. In other words, the light condensing unit 30 can condense the scattered or reflected light from the measurement target object on the light receiving lens 220 and also can obtain an image of a portion of the surface of the measurement target object.

[2.2. Light Condensing Effect]

Figure 9:
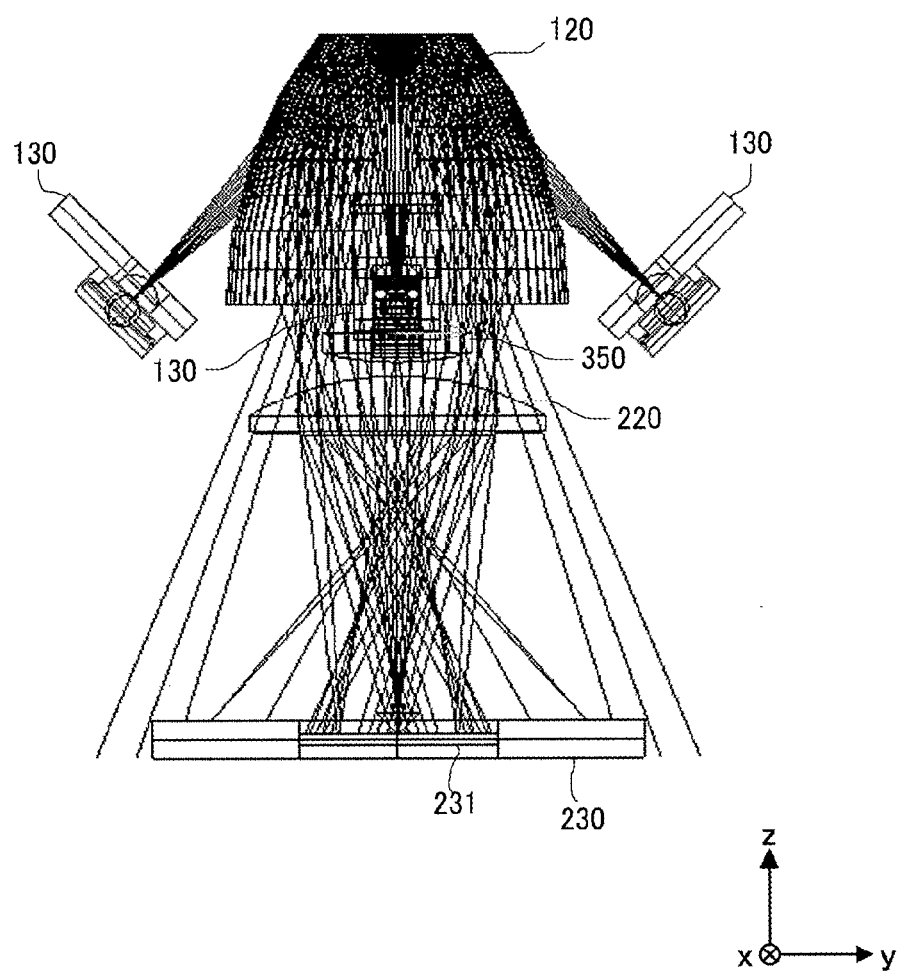
FIG. 9 is a schematic diagram illustrating results of ray-tracing simulation in the light condensing unit according to the second embodiment.

The light condensing effect of the light condensing unit 30 according to the second embodiment will be described with reference to FIG. 9. The description will be given of the light condensing effect of the light condensing unit 30 based on the results obtained by performing ray-tracing simulation on the light condensing unit 30 according to the second embodiment and the image sensor unit 20 equipped with the light condensing unit 30. FIG. 9 is a schematic diagram illustrating results obtained by performing ray-tracing simulation in the light condensing unit 30 according to the second embodiment. In the light condensing unit according to the second embodiment, the result obtained by the ray tracing without providing the reflection member and the collimating lens is similar to the result obtained by the ray tracing shown in FIG. 5, and thus the illustration thereof will be omitted.

A model of computation in the ray-tracing simulation shown in FIG. 9 is prepared based on the light condensing unit 30 and the image sensor module 20 shown in FIG. 8. In FIG. 9, for ease of understanding the ray-tracing results, the illustration of other components than the reflection member 120, the light irradiation member 130, the collimating lens 350, the light receiving lens 220, and the image sensor 230 included in the light condensing unit 30 and the image sensor module 20 is omitted. In the model of computation, the measurement target object 700 is placed on the upper portion of the upper opening portion 111. The measurement target object 700 is assumed to be a part of the human body, and a value of physical quantity corresponding to a part of the human body is assigned to the measurement target object 700 to allow the reflection, scattering, or the like of the light in the human body to be represented. In the model of computation, so as to more accurately simulate the reflection of light at the inner surface of the reflection member 120, the side wall of the reflection member 120 is divided into a plurality of grids, and thus the shape of the curved surface of the side wall is represented.

In the model of computation in the ray-tracing simulation, as an example of the specific configuration of the light condensing unit 30 and the image sensor module 20, the shape of each component or the distance between components is set to represent "the configuration in which light receiving lens 220 has a specification that forms an image of a subject with light coming from the middle to the far end (for example, approximately 20 to 30 centimeters), while the scattered or reflected light from the measurement target object 700 is applied to the light receiving lens 220 from a proximal end (for example, approximately one centimeter) relative to the middle or far end" described in the item [1.3. Shape of reflection member] described above. Furthermore, the shape and arrangement configuration of the collimating lens 350 are determined based on numerical values shown as the specific example in the item [2.1. Configuration of light condensing unit] described above. In FIG. 9, the shape of the reflection member 120 may be designed in a manner that the angle of incidence on the light receiving lens 220 of the light reflected by the inner surface of the reflection member 120 is smaller than the converging angle of the light receiving lens 220.

Referring to FIG. 9, we found that the scattered or reflected light from the measurement target object 700 is reflected by the inner surface of the reflection member 120 and most of the reflected light is condensed on the light receiving lens 220, which is similar to the result obtained by the ray tracing in the light condensing unit 10 according to the first embodiment. In addition, we found that most of the light incident on the light receiving lens 220 is incident on the light receiving surface 231 of the image sensor 230.

Moreover, in the light condensing unit 30, we found that the light passing through the collimating lens 350 forms an image on a partial region of the light receiving surface 231 of the image sensor 230. Referring to FIG. 9, a region (image formation region) in which the scattered or reflected light from the measurement target object 700 forms an image on the light receiving surface 231 is a region substantially near the center of the light receiving surface 231, as an example. Thus, in the image-forming region of the light receiving surface 231, an image may be obtained by capturing the surface of the measurement target object 700.

As described above with reference to FIG. 9, the use of the light condensing unit 30 according to the second embodiment makes it possible to further improve the light condensing efficiency on the light receiving unit connected to the light condensing unit 30. Thus, it is possible to improve the incidence efficiency on the light receiving surface 231 of the light receiving unit, for example, the image sensor module 20. Consequently, for example, the S/N ratio of the pixel signal obtained by the image sensor 230 is improved, and the detection of light is implemented with higher sensitivity.

Moreover, the light condensing unit 30 according to the second embodiment that is further equipped with the collimating lens 350 makes it possible to form an image obtained by capturing a portion of the surface of the measurement target object 700.

[2.3. Application Example]

An application example of the light condensing unit 30 according to the second embodiment will be described. As an application example, it is conceivable that the optical spectrum (three spectral values) of the scattered or reflected light from a part (skin) of the human body is obtained by the image sensor module 20, and the amount of melanin pigment or concentration of hemoglobin is estimated from the three spectral values, which is similar to the light condensing unit 10 according to the first embodiment.

Furthermore, the light condensing unit 30 including the collimating lens 350 makes it possible to form an image obtained by capturing a portion of the surface of the measurement target object 700. However, when the captured image is obtained, the light incident on the image-forming region from the surrounding region may be a noise. Thus, a captured image with higher quality may be obtained by performing a process of estimating a noise component from a pixel signal level in the region surrounding the image-forming region and removing the noise component.

As described above, in the light condensing unit 30 according to the second embodiment, based on the scattered or reflected light from a part (skin) of the human body, the amount of melanin pigment or concentration of hemoglobin of the part of the human body can be estimated, and an image obtained by capturing a portion of the surface of the human body can be formed. Thus, as an index for determining whether a user is in an excited condition as described in the application example of the light condensing unit 10 according to the first embodiment, it is possible to use various kinds of information obtained from the image of the body surface in addition to the information relating to the amount of melanin pigment or concentration of hemoglobin. For example, by observing color of the body surface or the state of sweating in the body surface from the image of the body surface, it is possible to further improve the determination accuracy of an excited condition.

<3. Third Embodiment>

The schematic configuration of a light condensing unit according to a third embodiment of the present disclosure will be described. The light condensing unit according to the third embodiment of the present disclosure has a configuration similar to the configuration of the light condensing unit according to the first embodiment described above, except that the light condensing unit according to the third embodiment includes a condensing lens and has a reflection member that is different in shape from the reflection member of the light condensing unit according to the first embodiment. Thus, the same configuration as the light condensing unit according to the first embodiment will be omitted in the following description of the light condensing unit according to the third embodiment, and the description will be given of the difference between them.

[3.1. Configuration of Light Condensing Unit]

The schematic configuration of the light condensing unit according to the third embodiment of the present disclosure will be first described with reference to FIG. 10. The light condensing unit according to the third embodiment is similar in appearance to the light condensing unit according to the first embodiment shown in FIG. 1, and thus description thereof will be omitted.

Figure 10:
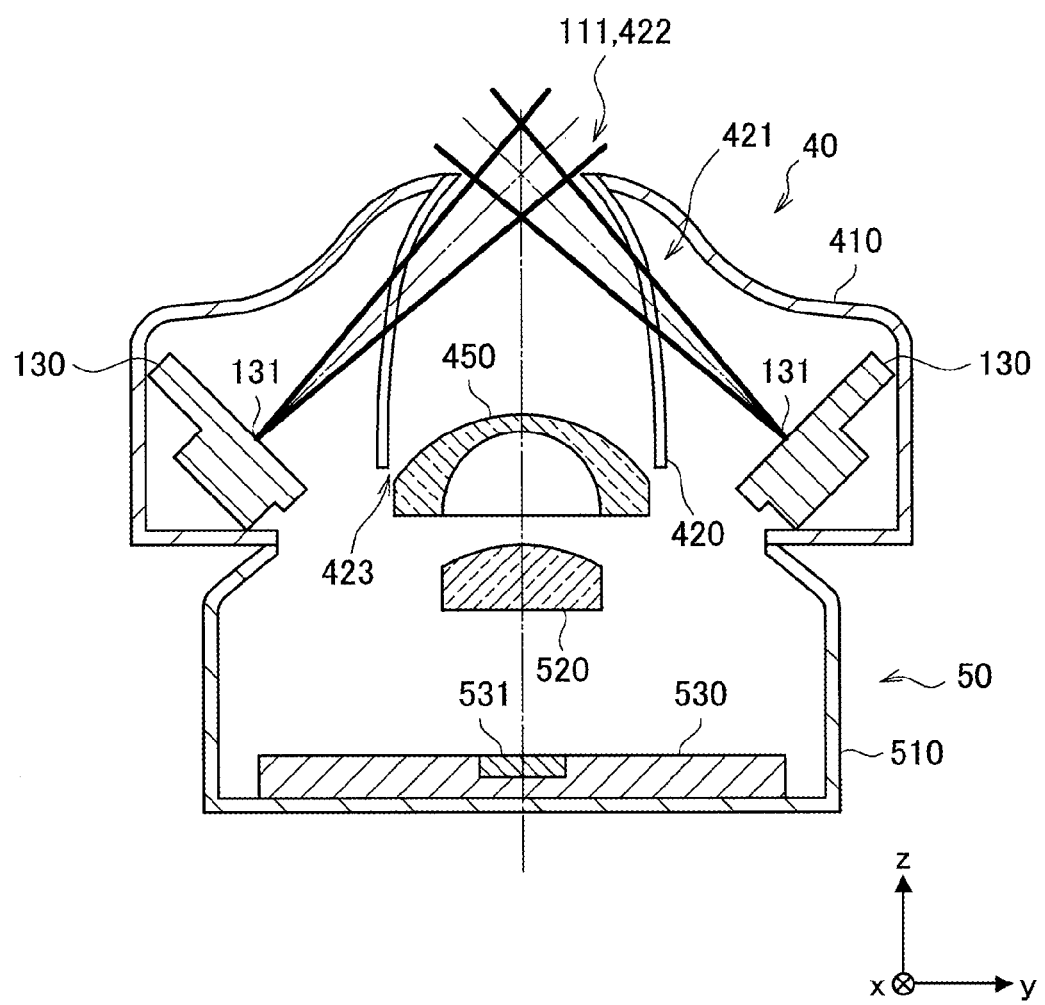
FIG. 10 is a sectional view of a light condensing unit according to a third embodiment of the present disclosure, taken along section A-A in FIG. 1.

FIG. 10 is a sectional view of the light condensing unit according to the third embodiment of the present disclosure, taken along section A-A in FIG. 1. FIG. 10 illustrates how to install a light condensing unit 40 according to the third embodiment of the present disclosure in an image sensor module 50.

The image sensor module 50 includes a housing 510, a light receiving lens 520, and an image sensor 530. In the image sensor module 50, the image sensor has a light receiving surface 531 that is smaller than that of the image sensor module 20 shown in FIGS. 2 and 8. With the decrease in size of the light receiving lens 520, accordingly the configuration of the housing 510 and the light receiving lens 520 are partially different from the configuration of the housing 210 and the light receiving lens 220 of the image sensor module 20, respectively.

The image sensor 530 has the light receiving surface 531 smaller in area than that of the image sensor 230 shown in FIGS. 2 and 8, as described above. The light receiving surface 531 may have a size of 3.6 (x-axis direction)×2.7 (y-axis direction) millimeters, as an example.

With the decrease in size of the light receiving lens 520, the light receiving lens 520 is formed to be different in a curvature and lens diameter from the light receiving lens 220 shown in FIGS. 2 and 8. The light receiving lens 520 has optimized curvature and refractive index in a manner to efficiently guide the light incident on the light receiving lens 520 to the light receiving surface 531 of the image sensor 530.

For example, the light receiving lens 520 may have a curvature of 0.2. In addition, for example, the light receiving lens 520 may have a lens diameter of 5 millimeters. Furthermore, the light receiving lens 520 may have substantially the same refractive index as the refractive index of the light receiving lens 220. For example, the light receiving lens 520 may have a refractive index of 1.8 to 1.9 for visible light. Moreover, the light receiving lens 520 may have a converging angle of approximately 18 degrees.

Furthermore, with the decrease in size of the light receiving lens 520, the housing 510 has a lower height in the z-axis direction than the housing 210 shown in FIGS. 2 and 8, that is, the distance between the light receiving lens 520 and the light receiving surface 531 is shorter than that of the housing 210.

The substantially central portion of the light receiving surface 531, the substantially central portion of the light receiving lens 520, and the substantially central portion of a light receiving opening portion 511 are arranged on the central axis c.

The light condensing unit 40 includes a housing 110, a reflection member 420, a light irradiation member 130, and a light condensing lens 450. The function and configuration of the housing 110 and the light irradiation member 130 are similar to the function and configuration of the housing 110 and the light irradiation member 130 of the light condensing unit 10 according to the first embodiment. In other words, the light condensing unit 40 is different from the light condensing unit 10 in that the reflection member 420 has a different shape and the light condensing lens 450 is further provided. The description will be given of the difference.

The shape of the reflection member 420 is determined depending on the lens characteristics of the light receiving lens 520. Specifically, the reflection member 420 has a dome shape, and its side wall is narrower in extent than the light condensing unit 10 according to the first embodiment and the light condensing unit 30 according to the second embodiment.

The shape of the reflection member 420 is determined based on an idea similar to the shape of the reflection member 120 described in the item [1.3. Shape of reflection member] described above. In other words, the shape of the reflection member 420 is designed depending on the converging angle of the light receiving lens 520. Specifically, the shape of the reflection member 420 is designed in a manner that the angle of incidence on the light receiving lens 520 of the light reflected by the inner surface of the reflection member 420 is smaller than the converging angle of the light receiving lens 520.

Other configurations of the reflection member 420 are similar to the reflection member 120 according to the first and second embodiments. In other words, a first opening portion 421, for example, having a slit shape is provided in the outer wall of the reflection member 420 at a portion corresponding to an irradiation region of the light irradiation member 130. The light emitted from the light irradiation member 130 is applied to the vicinity of the top of the reflection member 420 through the first opening portion 421 provided in the outer wall of the reflection member 420. A second opening portion 422 having a substantially circular shape is provided in the top portion of the reflection member 420, that is, the irradiation region. The bottom surface of the reflection member 420 is opened over the entire region and constitutes a third opening portion 423 having a substantially circular shape.

The light condensing unit 40 includes the light condensing lens 450 between the reflection member 420 and the light receiving lens 520. The light condensing lens 450 has a function of further condensing the light reflected by the inner surface of the reflection member 420 on the light receiving lens 520. In other words, the lens characteristics (curvature, refractive index, lens diameter, or the like) of the light condensing lens 450 may be determined depending on the lens characteristics of the light receiving lens 220.

For example, the light condensing lens 450 may be a spherical lens, and the light condensing lens 450 is arranged in a manner that the center of the light condensing lens 450 is positioned on the central axis c. The light condensing lens 450 is arranged at a position spaced apart from the light receiving lens 520 by a predetermined distance. The separation distance between the light condensing lens 450 and the light receiving lens 520 may be 3.5 millimeters, as an example. The light condensing lens 450 may have a diameter (lens diameter) of approximately 1.6 times greater than the diameter of the light receiving lens 520, as an example.

The light condensing lens 450 includes a convex lens formed on one surface and includes a concave lens formed on the other surface. The light condensing lens 450 is arranged in a manner that the surface on which the convex lens is formed faces the reflection member 420 and the surface on which the concave lens is formed faces the light receiving lens 520. The concave lens may have a curvature that is greater than a curvature of the convex lens.

Specifically, the convex lens of the light condensing lens 450 may have a diameter (lens diameter) of 8 millimeters, as an example. The convex lens of the light condensing lens 450 may have a curvature of 0.2, as an example.

Specifically, the concave lens of the light condensing lens 450 may have a diameter (lens diameter) of 5 millimeters, as an example. The concave lens of the light condensing lens 450 may have a curvature of 0.4, as an example.

The light condensing lens 450 may have a refractive index that is substantially similar to a refractive index of the light receiving lens 520. The refractive index of the light condensing lens 450 may be 1.8 to 1.9 for visible light, as an example.

A measurement target object may be placed on the upper portion of the upper opening portion 111 of the housing 110 of the light condensing unit 40, which is similar to the light condensing unit 10 according to the first embodiment.

With the configuration described above, in the light condensing unit 40, the scattered or reflected light from the measurement target object (irradiation light from the irradiation region) is reflected by the inner surface of the reflection member 420, passes through the light condensing lens 450, and is condensed on the light receiving lens 520. The shape of the reflection member 420 and the lens characteristics (curvature, refractive index, lens diameter, or the like) of the light condensing lens 450 are designed in a manner that the scattered or reflected light from the measurement target object (irradiation light from the irradiation region) is condensed on the light receiving lens 520. Thus, the light condensing unit 40 according to the third embodiment includes the reflection member 420 and the light condensing lens 450, and thus it is possible to condense the light efficiently on the light receiving lens 520 and the light receiving surface 531 which have a smaller size.

[3.2. Light Condensing Effect]

Figure 11:
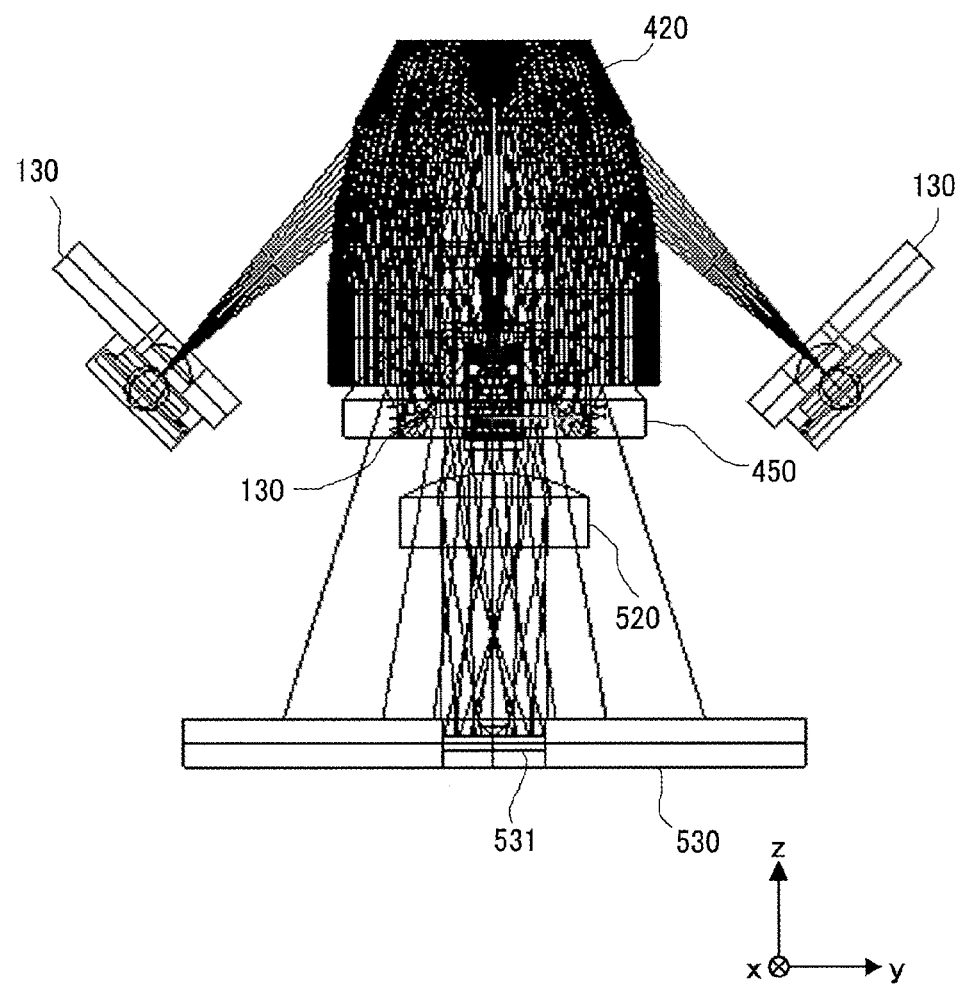
FIG. 11 is a schematic diagram illustrating results of ray-tracing simulation in a light condensing unit 40 according to the third embodiment.

The light condensing effect of the light condensing unit 30 according to the third embodiment will be described with reference to FIG. 11. The description will be given of the light condensing effect of the light condensing unit 40 based on the results obtained by performing ray-tracing simulation on the light condensing unit 40 according to the third embodiment and the image sensor unit 50 equipped with the light condensing unit 40. FIG. 11 is a schematic diagram illustrating results obtained by performing ray-tracing simulation in the light condensing unit 40 according to the third embodiment. In the light condensing unit 40, the result obtained by the ray tracing without providing the reflection member and the light condensing lens is different in the sizes of the light receiving lens 520 and the light receiving surface 531 of the image sensor 530, but substantially similar to the result obtained by the ray tracing shown in FIG. 5, and thus the illustration thereof will be omitted.

A model of computation in the ray-tracing simulation shown in FIG. 11 is prepared based on the light condensing unit 40 and the image sensor module 50 shown in FIG. 10. In FIG. 11, for ease of understanding the ray-tracing results, the illustration of other components than the reflection member 120, the light irradiation member 130, the light condensing lens 450, the light receiving lens 520, and the image sensor 530 included in the light condensing unit 40 and the image sensor module 50 is omitted. In the model of computation, the measurement target object 700 is placed on the upper portion of the upper opening portion 111. The measurement target object 700 is assumed to be a part of the human body, and a value of physical quantity corresponding to a part of the human body is assigned to the measurement target object 700 to allow the reflection, scattering, or the like of the light in the human body to be represented. In the model of computation, so as to more accurately simulate the reflection of light at the inner surface of the reflection member 420, the side wall of the reflection member 420 is divided into a plurality of grids, and thus the shape of the curved surface of the side wall is represented.

In the model of computation in the ray-tracing simulation, as an example of the specific configuration of the light condensing unit 40 and the image sensor module 50, the shape of each component or the distance between components is set to represent "the configuration in which light receiving lens 520 has a specification that forms an image of a subject with light coming from the middle to the far end (for example, approximately 20 to 30 centimeters), while the scattered or reflected light from the measurement target object 700 is applied to the light receiving lens 220 from a proximal end (for example, approximately one centimeter) relative to the middle or far end" described in the item [1.3. Shape of reflection member] described above. Furthermore, the shape and arrangement configuration of the light condensing lens 450, the light receiving lens 520, and the image sensor 530 are determined based on numerical values shown as the specific example in the item [3.1. Configuration of light condensing unit] described above. In FIG. 11, the shape of the reflection member 420 may be designed in a manner that the angle of incidence on the light receiving lens 520 of the light reflected by the inner surface of the reflection member 420 is smaller than the converging angle of the light receiving lens 520.

Referring to FIG. 11, the scattered or reflected light from the measurement target object 700 is reflected by the inner surface of the reflection member 420 and most of the reflected light is condensed on the light condensing lens 450, and thus we found that most of the reflected light is incident on the light receiving lens 520. In addition, we found that most of the light incident on the light receiving lens 520 is incident on the light receiving surface 531 of the image sensor 530. In other words, the light condensing unit 40 according to the third embodiment includes the reflection member 420 and the light condensing lens 450, and thus it is possible to condense the light efficiently on the light receiving lens 520 and the light receiving surface 531 which have a smaller size.

In the ray-tracing simulation shown in FIG. 11, we found that the incidence efficiency is improved by nearly two times, as compared to the case where the reflection member 420 and the light condensing lens 450 are not provided, from the result of the computation of incidence efficiency of the light on the light receiving surface 531 of the image sensor 530. It is apparent also from the results that the light condensing effect of the light condensing unit 40 according to the third embodiment can be achieved.

As described above with reference to FIG. 11, the use of the light condensing unit 40 according to the third embodiment makes it possible to further improve the light condensing efficiency on the light receiving unit connected to the light condensing unit 40. Thus, it is possible to improve the incidence efficiency on the light receiving surface 531 of the light receiving unit, for example, the image sensor module 50. Consequently, for example, the S/N ratio of the pixel signal obtained by the image sensor 530 is improved, and the detection of light is implemented with higher sensitivity.

As an application example of the light condensing unit 40 according to the third embodiment, the use that is similar to the application example of the light condensing unit 10 according to the first embodiment may be considered. In other words, the optical spectrum (three spectral values) of the scattered or reflected light from a part (skin) of the human body is obtained by the image sensor module 50, and the amount of melanin pigment or concentration of hemoglobin may be estimated from the three spectral values. Furthermore, the excited condition or the like of the subject may be determined based on information relating to the estimated amount of melanin pigment or concentration of hemoglobin.

<4. Modification>

The modification of the light condensing units 10, 30, and 40 according to the respective first, second, and third embodiments of the present disclosure will be described. In the following description of the modification, the description will be given by taking the light condensing unit 10 according to the first embodiment of the present disclosure as an example. However, the following modification is also applicable to the light condensing units 30 and 40 according to the second and third embodiments.

[4.1. Integration with Light Receiving Lens]

Figure 12:
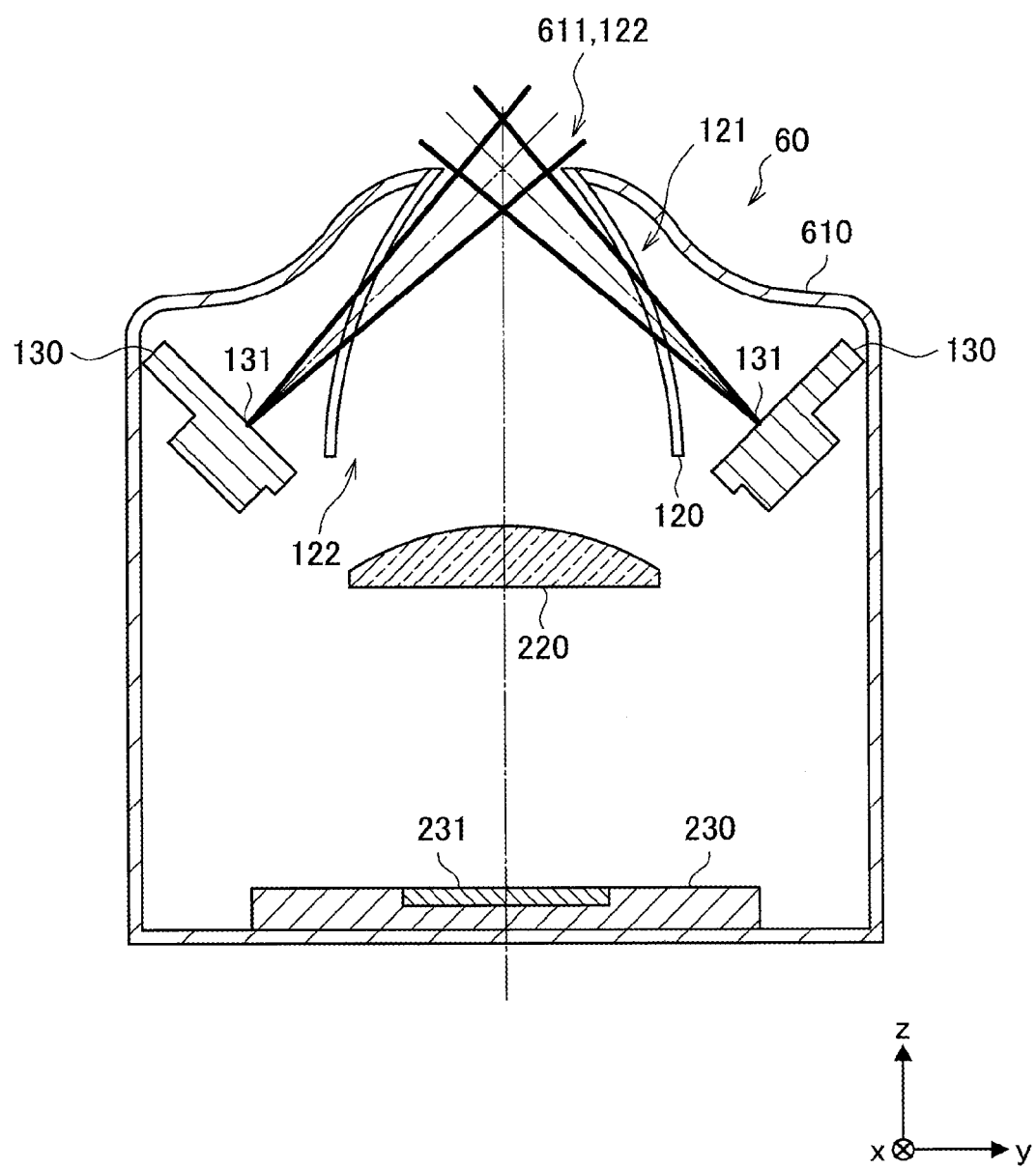
FIG. 12 is a sectional view illustrating a modification of the light condensing unit according to the first embodiment of the present disclosure, in which a light condensing unit is formed integrally with a light receiving unit.

The modification in which the light condensing unit 10 according to the first embodiment of the present disclosure and a light receiving unit are integrally formed will be described with reference to FIG. 12. FIG. 12 is a sectional view illustrating a modification of the light condensing unit according to the first embodiment of the present disclosure, in which a light condensing unit and a light receiving unit are integrally formed. FIG. 12 illustrates a sectional view in a plane formed by y-axis and z-axis through the central axis c of the light condensing unit according to the modification.

Referring to FIG. 12, a light condensing unit 60 according to the present modification includes a housing 610, a reflection member 120, a light irradiation member 130, a light receiving lens 220, and an image sensor 230. The function and configuration of the reflection member 120, the light irradiation member 130, the light receiving lens 220, and the image sensor 230 included in the light condensing unit 60 are similar to the respective components of the light condensing unit 10 according to the first embodiment described above, and thus the detailed description will be omitted.

In the example shown in FIG. 12, the housing 610 has a substantially cylindrical shape, and the substantially central portion of the upper portion of the housing 610 has a projection shape that projects toward the upward (positive direction of z-axis). An upper opening portion 611 that communicates the inner space of the housing 610 with the outside is provided in the distal end portion of the projection. The upper opening portion 611 is designed in a manner that the substantially central portion of the upper opening portion 611 falls in line with the central axis c.

As shown in FIG. 12, the reflection member 120, the light irradiation member 130, the light receiving lens 220, and the image sensor 230 within the housing 610 are arranged in a positional relationship similar to the positional relationship between components in the light condensing unit 10. In other words, in the light condensing unit 60, the light condensing unit and the light receiving unit are integrally formed.

As described above, the shape of the reflection member 120 is determined depending on the converging angle of the light receiving lens 220. Thus, for example, when the light condensing unit 10 according to the first embodiment is installed in an existing image sensor module 20, the lens characteristics such as a converging angle of the light receiving lens 220 of the image sensor module 20 is recognized in advance, and then it is necessary to design the shape of the reflection member 120 to match the characteristics.

On the other hand, in the light condensing unit 60 according to the present modification, the light condensing unit and the light receiving unit are integrally formed. Thus, the lens characteristics of the light receiving lens 220 and the shape of the reflection member 120 can be both designed, which leads to the improvement of the degree of freedom of design. Furthermore, the distance between the light receiving lens 220 and the light receiving surface 231 of the image sensor 230 or the distance between the light receiving lens 220 and the measurement target object placed on the upper opening portion 611 may be modified in an appropriate manner. Thus, the degree of freedom of design is further improved.

The reflection member 120, the light irradiation member 130, and the light receiving lens 220 are fixed to the inner walls of the housing 610 by a support member or the like, and thus the relative position between the three components is fixed. However, the material of the support member or the way to fix the reflection member 120, the light irradiation member 130, and the light receiving lens 220 is not particularly limited, but any material or way may be employed as long as the relative position between the reflection member 120, the light irradiation member 130, and the light receiving lens 220 is fixed.

[4.2. Change in Number of Light Irradiation Members]

Figure 13:
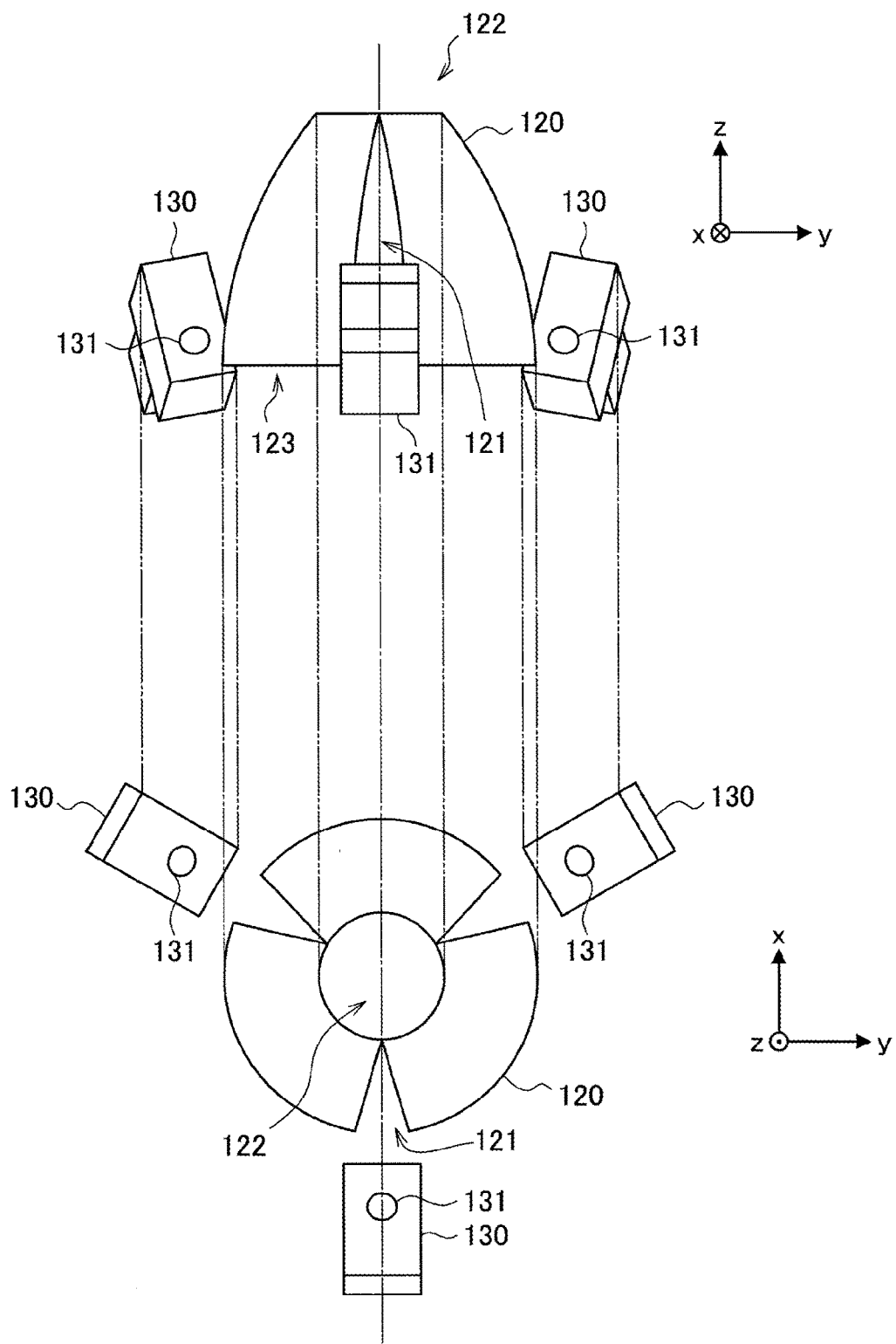
FIG. 13 is an explanatory diagram illustrated to describe a modification of the light condensing unit according to the first embodiment of the present disclosure, in which the number of light irradiation members is changed.

The modification in which the number of light irradiation members 130 is changed in the light condensing unit 10 according to the first embodiment of the present disclosure will be described with reference to FIG. 13. FIG. 13 is an explanatory diagram illustrated to describe the modification of the light condensing unit 10 according to the first embodiment of the present disclosure, in which the number of light irradiation members 130 is changed.

FIG. 13 illustrates only the reflection member 120 and the light irradiation member 130 among components in a light condensing unit 70 according to the present modification. FIG. 13 illustrates the side view of the reflection member 120 and the top view of the light irradiation member 130 in a manner that the positions of the two members are associated with each other. The light condensing unit 70 according to the present modification has the same configuration as the light condensing unit 10 according to the first embodiment, except that the number of the light irradiation members 130 is different, and thus the detailed description of the same configuration will be omitted.

Referring to FIG. 13, three light irradiation members 130 are provided in the light condensing unit 70 according to the present modification, while four light irradiation members 130 are provided in the light condensing unit 10 according to the first embodiment. The three light irradiation members are arranged around the outer wall of the reflection member 120 at substantially equal intervals from each other, that is, 120-degree intervals.

As shown in the present modification, even when three light irradiation members 130 are provided, it is possible to perform an application example in which the optical spectrum of the scattered or reflected light is obtained by condensing the scattered or reflected light from the measurement target object on the light receiving lens of the image sensor module, as described in the item [1.5. Application example] described above. In this way, in the light condensing unit 10 according to the first embodiment, a plurality of the light irradiation members 130 may be arranged, and the number of the light irradiation members is not limited. However, it is preferable that at least three light irradiation members 130 are provided to measure the physical characteristics of the measurement target object with higher accuracy.

[4.3. Other Modifications]

The light condensing unit 10 according to the first embodiment of the present disclosure can further have the following configuration.

For example, the light condensing unit 10 according to the first embodiment may be provided with an external light source. When an external light source is provided, the light irradiation member 130 arranged in the housing may be configured without a function of a light source or may be configured without a function of light irradiation in a predetermined direction. Specifically, in the light condensing unit according to the present modification, the light source provided outside the housing and the light irradiation member arranged inside the housing are connected to each other by any light guiding medium, and the light irradiation member may irradiate the irradiation region with the light from the light source guided by the light guiding medium. The light guiding medium may be an optical fiber or a light guide plate, as an example. The external light source may be a flash of a camera unit in which an image sensor module is incorporated or an external lamp, as an example.

For example, the light receiving unit equipped with the light condensing unit 10 according to the first embodiment may not be an image sensor module. For example, the light receiving unit may include any photodetector in which an imaging function is not provided, that is, light receiving elements are not arranged in an array. For example, in the case of the application example described in the item [1.5. Application example] described above, it is sufficient to obtain the optical spectrum of the scattered or reflected light from the measurement target object, and it is not necessarily to obtain a captured image. Thus, even when the light receiving unit is not provided with an image sensor but is provided with any photodetector, it is possible to implement the application example.

<5. General Versatility of Reflection Member>

The general versatility of the reflection members 120 and 420 included in the light condensing units 10, 30, and 40 according to the respective first, second, and third embodiments will be described.

As described in the above item [1.3. Shape of reflection member], the shape of the reflection members 120 and 420 according to the first, second, and third embodiments is designed depending on the converging angle of the light receiving lenses 220 and 520 of the light receiving unit equipped with the light condensing unit 10, 30, and 40. The results obtained by checking the general versatility of the reflection member to the light receiving lens having different converging angles will be described.

Figure 14:
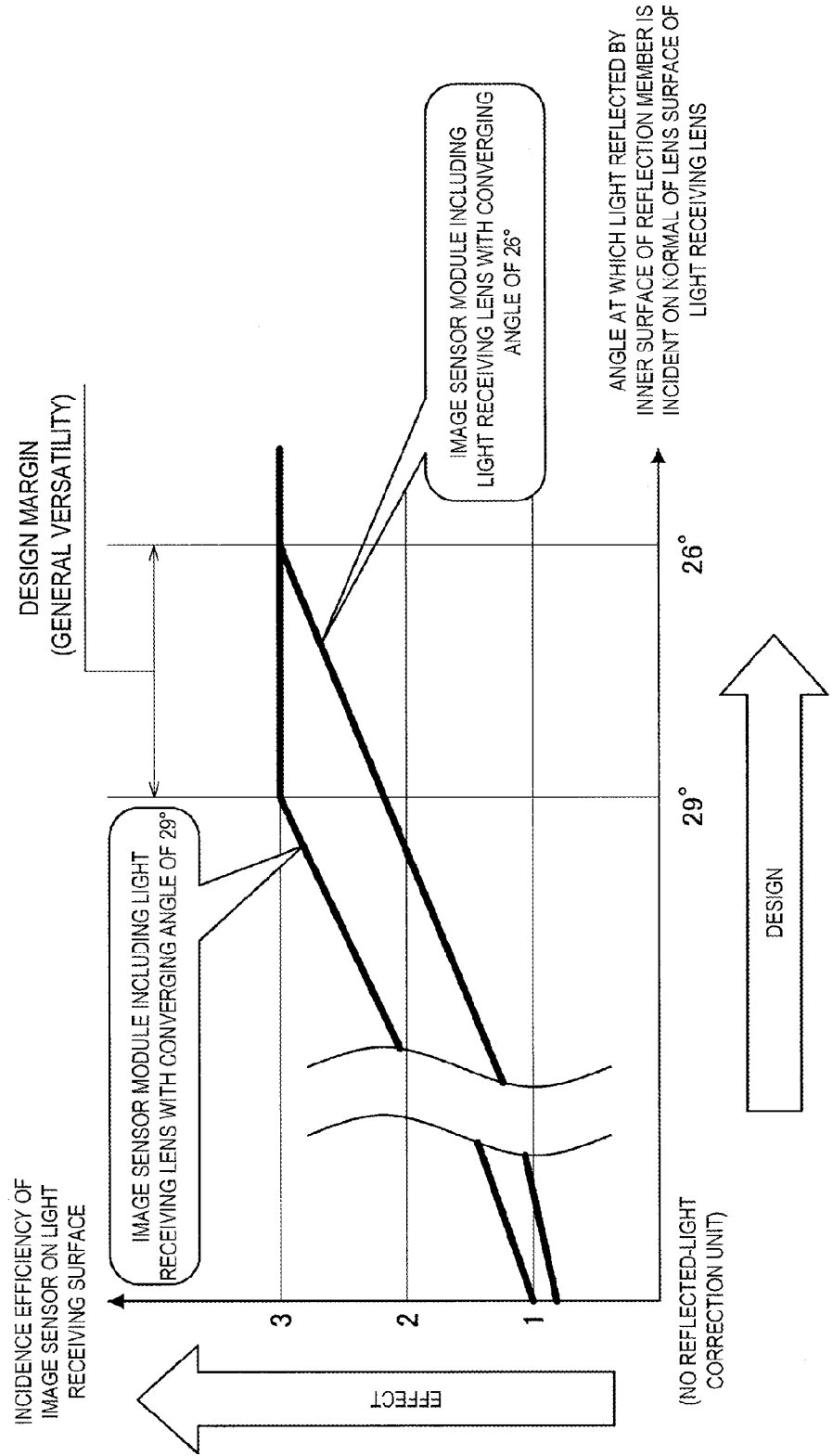
FIG. 14 is an explanatory diagram illustrated to describe general versatility of the reflection member to the light receiving lens having a relatively large converging angle.

The general versatility of the reflection member to the light receiving lens having a relatively large converging angle will be described with reference to FIG. 14. FIG. 14 is an explanatory diagram illustrated to describe general versatility of the reflection member to the light receiving lens having a relatively large converging angle.

In the graph shown in FIG. 14, the horizontal axis represents an angle at which the light reflected by an inner surface of a reflection member is incident on a normal of a lens surface of a light receiving lens. In other words, the horizontal axis corresponds to an angle of incidence on a light receiving lens of the light reflected by an inner surface of a reflection member. In the following description, the angle shown in the horizontal axis is simply referred to as "angle of incidence".

In the graph shown in FIG. 14, the vertical axis represents incidence efficiency of an image sensor on a light receiving surface. However, incidence efficiency is defined by normalizing the incidence efficiency when a reflection member is not provided in an image sensor module including a light receiving lens having a converging angle of 29 degrees to 1. In the following description, the incidence efficiency shown in the vertical axis is simply referred to as "incidence efficiency".

In the graph shown in FIG. 14, two relationships are shown. In the graph, the line on the upper side represents the relationship between angle of incidence and incidence efficiency for an image sensor module including a light receiving lens having a converging angle of 29 degrees. In the graph, the line on the lower side represents the relationship between angle of incidence and incidence efficiency for an image sensor module including a light receiving lens having a converging angle of 26 degrees. The light receiving lens having a converging angle of 29 degrees corresponds to an example of the specifications of the light receiving lens 220 of the image sensor module 20 described in the first and second embodiments of the present disclosure.

Referring to FIG. 14, in the image sensor module including a light receiving lens having a converging angle of 29 degrees, as described above, the incidence efficiency when a reflection member is not provided is normalized to 1. As a reflection member is provided and an angle of incidence on a light receiving lens is reduced by a change in the shape of the reflection member, the incidence efficiency gradually increases. The point where the angle of incidence is less than or equal to the converging angle, that is, the angle of incidence is 29 degrees shows that the incidence efficiency is approximately three times greater than that when a reflection member is not provided. If once the angle of incidence is less than or equal to the converging angle, even though the angle of incidence is further reduced by a further change in the shape of the reflection member, the incidence efficiency is not increased further.

On the other hand, in the image sensor module including a light receiving lens having a converging angle of 26 degrees, the incidence efficiency when a reflection member is not provided is slightly lower than when a light receiving lens has a converging angle of 29 degrees because the converging angle is made to be smaller. As a reflection member is provided and an angle of incidence on a light receiving lens is reduced by a change in the shape of the reflection member, the incidence efficiency gradually increases. The point where the angle of incidence is less than or equal to the converging angle, that is, the angle of incidence is 26 degrees shows that the incidence efficiency is approximately three times greater than that when a reflection member is not provided.

For example, the angle of incidence on the light receiving lens is designed to be 29 degrees in designing the shape of the reflection member. In this case, as described above, in the image sensor module including a light receiving lens having a converging angle of 29 degrees, it is possible to improve the incidence efficiency by approximately three times. On the other hand, in the image sensor module including a light receiving lens having a converging angle of 26 degrees, although the angle of incidence is greater than the converging angle only by 3 degrees, it is possible to improve the incidence efficiency by two times. In other words, even when a reflection member designed to have an angle of incidence of 29 degrees, that is, designed to be corresponded to the light receiving lens having a converging angle of 29 degrees is installed in an image sensor module including a light receiving lens having a converging angle of 26 degree, it is possible to obtain effect of improving the incidence efficiency by more than double.

Thus, the reflection member has a margin of approximately 3 degrees to the angle of incidence on the light receiving lens with respect to the light receiving lens having a relatively large converging angle of approximately 29 degrees, and thus the reflection member can be used for general purposes.

Figure 15:
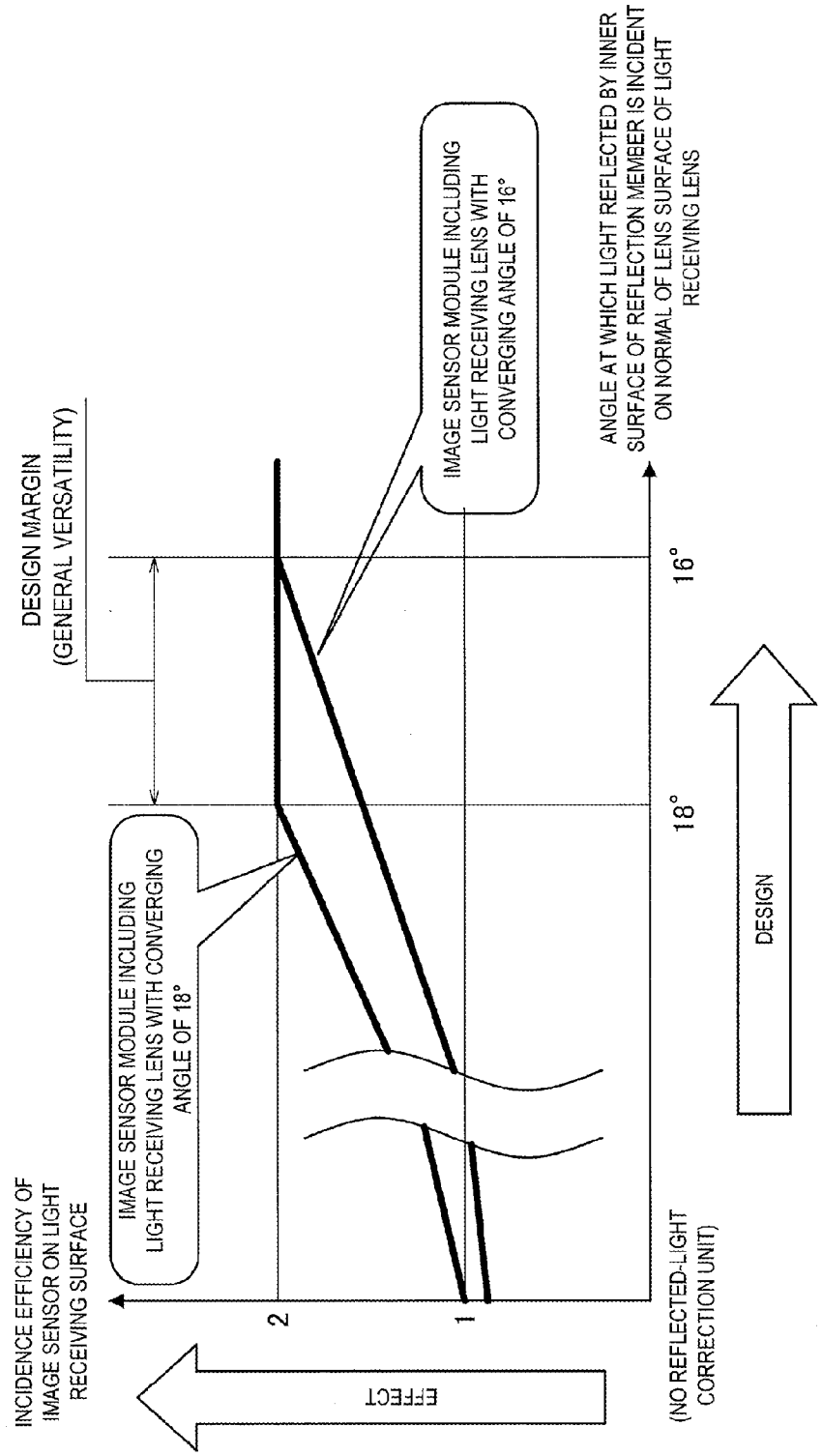
FIG. 15 is an explanatory diagram illustrated to describe general versatility of the reflection member to the light receiving lens having a relatively small converging angle.

The general versatility of the reflection member to a light receiving lens having a relatively small converging angle will be described with reference to FIG. 15. FIG. 15 is an explanatory diagram illustrated to describe general versatility of the reflection member to a light receiving lens having a relatively small converging angle.

The horizontal and vertical axes in FIG. 15 represent the same physical quantity as the horizontal and vertical axes in FIG. 14. However, the incidence efficiency shown in the vertical axis of FIG. 15 is defined by normalizing the incidence efficiency when a reflection member is not provided in an image sensor module including a light receiving lens having a converging angle of 18 degrees to 1.

In the graph shown in FIG. 15, two relationships are shown. In the graph, the line on the upper side represents the relationship between angle of incidence and incidence efficiency for an image sensor module including a light receiving lens having a converging angle of 18 degrees. In the graph, the line on the lower side represents the relationship between angle of incidence and incidence efficiency for an image sensor module including a light receiving lens having a converging angle of 16 degrees. The light receiving lens having a converging angle of 18 degrees corresponds to an example of the specifications of the light receiving lens 520 of the image sensor module 50 described in the third embodiment of the present disclosure.

Referring to FIG. 15, in the image sensor module including a light receiving lens having a converging angle of 18 degrees, as described above, the incidence efficiency when a reflection member is not provided is normalized to 1. As a reflection member is provided and an angle of incidence on a light receiving lens is reduced by a change in the shape of the reflection member, the incidence efficiency gradually increases. The point where the angle of incidence is less than or equal to the converging angle, that is, the angle of incidence is 18 degrees shows that the incidence efficiency is approximately two times greater than that when a reflection member is not provided. If once the angle of incidence is less than or equal to the converging angle, even though the angle of incidence is further reduced by a further change in the shape of the reflection member, the incidence efficiency is not increased further.

On the other hand, in the image sensor module including a light receiving lens having a converging angle of 16 degrees, the incidence efficiency when a reflection member is not provided is slightly lower than when a light receiving lens has a converging angle of 18 degrees because the converging angle is made to be smaller. As a reflection member is provided and an angle of incidence on a light receiving lens is reduced by a change in the shape of the reflection member, the incidence efficiency gradually increases. The point where the angle of incidence is less than or equal to the converging angle, that is, the angle of incidence is 18 degrees shows that the incidence efficiency is approximately two times greater than that when a reflection member is not provided.

For example, the angle of incidence on the light receiving lens is designed to be 18 degrees in designing the shape of the reflection member. In this case, as described above, in the image sensor module including a light receiving lens having a converging angle of 18 degrees, it is possible to improve the incidence efficiency by approximately two times. On the other hand, in the image sensor module including a light receiving lens having a converging angle of 16 degrees, although the angle of incidence is greater than the converging angle only by 2 degrees, it is possible to improve the incidence efficiency by 1.5 times. In other words, even when a reflection member designed to have an angle of incidence of 18 degrees, that is, designed to be corresponded to the light receiving lens having a converging angle of 18 degrees is installed in an image sensor module including a light receiving lens having a converging angle of 16 degree, it is possible to obtain effect of improving the incidence efficiency by more than 1.5 times.

Thus, the reflection member has a margin of approximately 2 degrees to the angle of incidence on the light receiving lens with respect to the light receiving lens having a relatively small converging angle of approximately 18 degrees, and thus the reflection member can be used for general purposes.

The general versatility of the reflection members 120 and 420 included in the light condensing units 10, 30, and 40 according to the respective first, second, and third embodiments of the present disclosure has been described with reference to FIGS. 14 and 15. As described above, although the shape of the reflection members 120 and 420 according to the first, second, and third embodiments is determined depending on the converging angle of the light receiving lenses 220 and 520, respectively, a certain degree of general versatility is achieved. Thus, even when the light condensing unit 10, 30, or 40 is installed in an existing image sensor module, it is possible to improve the light condensing efficiency without a change in the shape of the reflection member 120 or 420 in a rigorous manner.

<6. Conclusion>

As described above, the light condensing unit 10 according to the first embodiment of the present disclosure provides the following effects.

The light condensing unit 10 according to the first embodiment includes the reflection member 120 and the plurality of light irradiation members 130. The reflection member 120 has a dome shape, and the inner surface of the reflection member 120 is a mirror-finished surface. The light irradiation member 130 is arranged around the reflection member 120. The light emitted from the light irradiation member 130 is applied to the irradiation region of the top portion of the reflection member 120 through the first opening portion 121 provided in the side wall of the reflection member 120. The measurement target object is arranged in contact with the irradiation region, for example, the upper portion of the second opening portion 122, and the light emitted from the light irradiation member 130 is reflected from the surface of the measurement target object or is scattered within the measurement target object. The scattered or reflected light from the measurement target object is reflected by the inner surface of the reflection member 120, passes through the third opening portion 123 provided on the bottom surface of the reflection member 120, and is incident on the light receiving lens 220 of the light receiving unit, for example, the image sensor module 20 provided to face the third opening portion 123.

In this case, the shape of the reflection member 120 is designed depending on the converging angle of the light receiving lens 220. Specifically, the shape of the reflection member 120 is designed in a manner that the angle of incidence on the light receiving lens 220 of the light reflected by the inner surface of the reflection member 120 is smaller than the converging angle of the light receiving lens 220. Thus, the scattered or reflected light from the measurement target object can be incident on the light receiving lens 220 at an angle of incidence that is smaller than the converging angle of the light receiving lens 220 by allowing the scattered or reflected light to be reflected by the inner surface of the reflection member 120, thereby achieving the improved light condensing efficiency.

Furthermore, in the light condensing unit 10 according to the first embodiment, the reflection member 120 may have a shape designed in a manner that the scattered or reflected light from the measurement target object located in a proximal end is incident on the light receiving lens 220 at an angle of incidence that is equal to the image-forming light coming from the middle to the far end by reflecting the scattered or reflected light by the inner wall of the reflection member 120. In other words, even when the light receiving lens 220 has a specification that forms an image of a subject with light at a relatively far distance of the middle to the far end (for example, approximately 20 to 30 centimeters) and the scattered or reflected light from the measurement target object is applied to the light receiving lens 220 from a proximal end (for example, approximately 1 centimeter) relative to the middle or far end, the irradiation light coming from the distance corresponding to the so-called close-up shot can be condensed in a more efficient manner.

As an application example of the light condensing lens 10 according to the first embodiment, it is considered that the light condensing unit 10 is installed in the image sensor module 20, and the optical spectrum of the scattered or reflected light from a part (skin) of the human body as the measurement target object 700 is measured by the image sensor module 20. It is possible to estimate the amount of melanin pigment in the epidermis and the concentration of hemoglobin in the red blood cells of the subject based on the optical spectrum. Furthermore, the mental condition of the subject, for example, whether the subject is in excited condition is determined based on the estimated amount of melanin pigment and concentration of hemoglobin in the red blood cells. Thus, for example, in viewing video content or playing game content, the excited condition of the viewer or user is estimated by the way described above, and a change in the contents of game or video content depending on the excited condition can provide a viewing and operation experience with a sense of presence for the viewer or user.

The light condensing unit 30 according to the second embodiment of the present disclosure further includes the collimating lens 350 between the reflection member 120 and the light receiving lens 220, in addition to the configuration of the light condensing unit 10 according to the first embodiment.

The collimating lens 350 constitutes a collimator by making a pair with the light receiving lens 220, corrects a portion of the scattered or reflected light from the measurement target object (irradiation light from the irradiation region) to produce parallel light, and then allows the parallel light to be incident on the light receiving surface 231 of the image sensor 230 included in the image sensor module 20. Thus, the light condensing unit 30 including the collimating lens 350 allows a portion of the scattered or reflected light from the measurement target object (irradiation light from the irradiation region) to form an image on the light receiving cell surface of the image sensor 230. Hence, the light condensing unit 30, which further includes the collimating lens 350, has an imaging function of capturing a portion of the surface of the measurement target object in addition to the function of condensing the scattered or reflected light from the measurement target object.

Thus, as an index for determining whether a user is in an excited condition as described in the application example of the light condensing unit 10 according to the first embodiment, it is possible to use various kinds of information obtained from the image of the body surface in addition to the information relating to the amount of melanin pigment or concentration of hemoglobin. For example, by observing color of the body surface or the state of sweating in the body surface from the image of the body surface, it is possible to further improve the determination accuracy of an excited condition.

The light condensing unit 40 according to the third embodiment of the present disclosure includes the reflection member 420 instead of the reflection member 120 and further includes the light condensing lens 450 between the light receiving lens 220 and the reflection member 420, which is different from the configuration of the light condensing unit 10 according to the first embodiment. The reflection member 420 has a side wall that is made to be narrower than that of the reflection member 120.

The light condensing unit 40 having the configuration described above allows the light to be condensed efficiently on the image sensor module 50 including a small image sensor. In other words, in the light condensing unit 40, the scattered or reflected light from the measurement target object (irradiation light from the irradiation region) is reflected by the inner surface of the reflection member 420, passes through the light condensing lens 450, and is condensed on the light receiving lens 520 of the image sensor module 50. Thus, the light condensing unit 40 according to the third embodiment includes the reflection member 420 and the light condensing lens 450, and thus it is possible to condense the light efficiently on the light receiving lens 520 and the light receiving surface 531 which have a smaller size.

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, in the embodiments described above, although there has been described the case in which the light irradiation member included in the light condensing unit emits white light, the present technology is not limited thereto. For example, a plurality of light irradiation members may emit light of different wavelengths. In addition, when a plurality of light irradiation members emit light of different wavelengths, an image sensor of an image sensor module included in the light condensing unit may not be provided with a color filter. In other words, a first light irradiation member emits light of a first wavelength, and thus an image sensor can obtain optical spectrum of the scattered or reflected light from the measurement target object corresponding to the light of the first wavelength. Thus, a plurality of light irradiation members emit light having different wavelengths in a sequential manner and an image sensor obtains optical spectrum every time the light is emitted, and consequently it is possible to obtain optical spectrum of the scattered or reflected light from the measurement target object.

For example, in the embodiments described above, although there has been described the case in which three color filters of R, G, and B are provided in the image sensor of the image sensor module, the present technology is not limited thereto. For example, the image sensor may be provided with a color filter of yellow (Y) in addition to R, G, and B. If the image sensor further includes a color filter of yellow (Y), it is possible for the image sensor to obtain four spectral values as optical spectra of the scattered or reflected light from the measurement target object. A spectral value corresponding to yellow (Y) color is well corresponded to the spectral reflectance curve of the skin of the human body. Thus, when the amount of melanin pigment or concentration of hemoglobin of the subject is estimated from data corresponding to the spectral reflectance curve of the skin of the human body, it is possible to improve the accuracy of estimation by using four spectral values of R, G, B, and Y.

For example, in the embodiments described above, although there has been described the case in which the first opening portion formed in the light irradiation member included in the light condensing unit has a slit shape, the present technology is not limited thereto. The first opening portion may have other shapes than a slit such as circular or polygonal, as long as the light from the light irradiation member is not prevented from being applied on the irradiation region.

For example, in the embodiments described above, although there has been described the case in which the measurement target object placed on the upper opening portion of the light condensing unit is a part of the human body, the present technology is not limited thereto. The measurement target object on which the light condensing unit according to the present exemplary embodiment is applied includes, but is not limited to a human being, a living body. In the present exemplary embodiment, it is possible to obtain optical spectrum of any measurement target object, for example, by using an image sensor module as a light receiving unit.

Additionally, the present technology may also be configured as below.

(1)

A light condensing unit including:

a reflection member having a hollow dome shape a side wall of which is curved to be extended from a top portion toward a bottom portion, the reflection member having a mirror-finished inner surface; and a plurality of light irradiation members arranged around an outer wall of the reflection member and configured to irradiate an irradiation region of the top portion with light through a first opening portion formed in the outer wall, wherein the reflection member includes a second opening portion formed in the irradiation region of the top portion, and a third opening portion formed in the bottom portion to face a light receiving lens of a light receiving unit, the light receiving unit being configured to perform a predetermined process on received light, and wherein the reflection member guides light coming from the irradiation region and being reflected by the inner surface to the light receiving lens.

(2)

The light condensing unit according to (1), wherein the reflection member has an inner shape formed in a manner that an angle of incidence of light coming from the irradiation region on the light receiving lens is less than or equal to an angle greater than a converging angle of the light receiving lens by a predetermined angle.

(3)

The light condensing unit according to (1) or (2), wherein the reflection member has an inner shape formed in a manner that an angle of incidence of light coming from the irradiation region on the light receiving lens is less than or equal to a converging angle of the light receiving lens.

(4)

The light condensing unit according to any one of (1) to (3), further including:

a light path adjusting unit between the second opening portion of the reflection member and the light receiving lens.

(5)

The light condensing unit according to (4), wherein the light path adjusting unit is a collimating lens, and wherein the collimating lens and the light receiving lens constitute a collimator configured to correct light coming from the irradiation region and being reflected by the inner surface of the reflection member to produce parallel light.

(6)

The light condensing unit according to (5), wherein a surface of the collimating lens facing the light receiving lens has a curvature substantially equal to a curvature of the light receiving lens.

(7)

The light condensing unit according to (4), wherein the light path adjusting unit is a light condensing lens, and wherein a concave lens is formed on a surface of the light condensing lens facing the light receiving lens and a convex lens is formed on a surface of the light condensing lens facing the second opening portion.

(8)

The light condensing unit according to (7), wherein the concave lens has a curvature greater than a curvature of the convex lens.

(9)

The light condensing unit according to any one of (1) to (8), wherein the plurality of light irradiation members are arranged around the outer wall of the reflection member at substantially equal intervals from each other, and wherein the plurality of light irradiation members have optical axes intersecting with each other substantially at a center of the irradiation region.

(10)

The light condensing unit according to any one of (1) to (9), further including: a housing formed by a light shielding member, the housing having an inner space for accommodating the reflection member and the light irradiation member, wherein the housing has an opening portion formed at each position corresponding to the first opening portion and the second opening portion.

(11)

The light condensing module according to any one of (1) to (10), wherein a measurement target object is placed on the irradiation region, the measurement target object being at least a part of a living body, and wherein the light irradiation member irradiates the measurement target object with light.

(12)

The light condensing unit according to any one of (1) to (11), wherein the light receiving unit is an image sensor module configured to output a pixel signal depending on an amount of received light.

(13)

The light condensing unit according to (12), wherein an optical spectrum of light coming from the irradiation region is calculated based on the pixel signal outputted from the image sensor module.

(14)

The light condensing unit according to (10), wherein the housing is formed integrally with the light receiving unit.

(15)

The light condensing module according to (10), further including:

a light source provided outside the housing; and a light guiding medium configured to guide light from the light source to the light irradiation member, wherein the light irradiation member irradiates the irradiation region with the light guided by the light guiding medium from the light source.

(16)

The light condensing unit according to any one of (1) to (15), wherein the first opening portion is a slit formed in a direction from the top portion of the reflection member toward the bottom portion of the reflection member.

(17)

The light condensing unit according to any one of (1) to (16), wherein three or more of the light irradiation members are provided.

(18)

The light condensing unit according to any one of (1) to (17), wherein the light irradiation member has an LED that emits white light.

(19)

A light condensation method including:

irradiating an irradiation region with light through a first opening portion by a plurality of light irradiation members, the light irradiation members being arranged around an outer wall of a reflection member, the reflection member having a hollow dome shape a side wall of which is curved to be extended from a top portion toward a bottom portion, the reflection member having a mirror-finished inner surface, the first opening portion being formed in the outer wall, the irradiation region being positioned on the top portion;

reflecting irradiation light from the irradiation region by the inner surface and guiding the reflected light to a second opening portion formed in the bottom portion of the reflection member; and allowing the guided light to be incident on a light receiving lens of an image sensor module, the image sensor module being configured to output a pixel signal depending on an amount of received light, the light receiving lens being provided to face the second opening portion.

(20)

A light detection system including:

an image sensor module provided with a light receiving lens and configured to output a pixel signal depending on an amount of received light through the light receiving lens; and a light condensing unit configured to condense light on the light receiving lens, wherein the light condensing unit includes a reflection member having a hollow dome shape a side wall of which is curved to be extended from a top portion toward a bottom portion, the reflection member having a mirror-finished inner surface, and a plurality of light irradiation members arranged around an outer wall of the reflection member and configured to irradiate an irradiation region of the top portion with light through a first opening portion formed in the outer wall, wherein the reflection member includes a second opening portion formed in the irradiation region of the top portion, and a third opening portion formed in the bottom portion to face a light receiving lens of a light receiving unit, the light receiving unit being configured to perform a predetermined process on received light, and wherein the reflection member guides light coming from the irradiation region and being reflected by the inner surface to the light receiving lens.

REFERENCE SIGNS LIST

10, 30, 40, 60, 70 light condensing unit
20, 50 image sensor module
110, 210, 510, 610 housing
120, 420 reflection member
130 light irradiation member
220, 520 light receiving lens
230, 530 image sensor
231, 531 light receiving surface
350 collimating lens
450 light condensing lens

The invention claimed is:

1. A light condensing unit comprising:

a reflection member having a hollow dome shape, a side wall of the dome shape being curved to be extended from a top portion toward a bottom portion, the reflection member having a mirror-finished inner surface;

a plurality of light irradiation members arranged around an outer wall of the reflection member and configured to irradiate an irradiation region of the top portion with light through a first opening portion formed in the outer wall, wherein the reflection member includes
a second opening portion formed in the irradiation region of the top portion, and
a third opening portion formed in the bottom portion to face a light receiving lens of a light receiving unit, the light receiving unit being configured to perform a predetermined process on received light, and
wherein the reflection member guides light coming from the irradiation region and being reflected by the inner surface to the light receiving lens; and
a collimating lens between the second opening portion of the reflection member and the light receiving lens, and
wherein the collimating lens and the light receiving lens constitute a collimator configured to correct light coming from the irradiation region and being reflected by the inner surface of the reflection member to produce parallel light.

2. The light condensing unit according to claim 1, wherein the reflection member has an inner shape formed in a manner that an angle of incidence of light coming from the irradiation region on the light receiving lens is less than or equal to an angle that is three degrees greater than a converging angle of the light receiving lens.

3. The light condensing unit according to claim 1, wherein the reflection member has an inner shape formed in a manner that an angle of incidence of light coming from the irradiation region on the light receiving lens is less than or equal to a converging angle of the light receiving lens.

4. The light condensing unit according to claim 1, wherein a surface of the collimating lens facing the light receiving lens has a curvature substantially equal to a curvature of the light receiving lens.

5. The light condensing unit according to claim 1, wherein the plurality of light irradiation members are arranged around the outer wall of the reflection member at substantially equal intervals from each other, and
wherein the plurality of light irradiation members have optical axes intersecting with each other substantially at a center of the irradiation region.

6. The light condensing unit according to claim 1, further comprising:
a housing formed by a light shielding member, the housing having an inner space for accommodating the reflection member and the light irradiation members,
wherein the housing has an opening portion formed at each position corresponding to the second opening portion and the third opening portion of the reflection member.

7. The light condensing unit according to claim 6, wherein the housing is formed integrally with the light receiving unit.

8. The light condensing module according to claim 1, wherein a measurement target object is placed on the irradiation region, the measurement target object being at least a part of a living body, and
wherein the light irradiation member irradiates the measurement target object with light.

9. The light condensing unit according to claim 1, wherein the light receiving unit is an image sensor module configured to output a pixel signal depending on an amount of received light.

10. The light condensing unit according to claim 9, wherein an optical spectrum of light coming from the irradiation region is calculated based on the pixel signal outputted from the image sensor module.

11. The light condensing unit according to claim 1, wherein the first opening portion is a slit formed in a direction from the top portion of the reflection member toward the bottom portion of the reflection member.

12. The light condensing unit according to claim 1, wherein three or more of the light irradiation members are provided.

13. The light condensing unit according to claim 1, wherein the light irradiation member has an light emitting diode (LED) that emits white light.

14. A light condensing unit, comprising:
a reflection member having a hollow dome shape, a side wall of the dome shape being curved to be extended from a top portion toward a bottom portion, the reflection member having a mirror-finished inner surface;
a plurality of light irradiation members arranged around an outer wall of the reflection member and configured to irradiate an irradiation region of the top portion with light through a first opening portion formed in the outer wall,
wherein the reflection member includes
a second opening portion formed in the irradiation region of the top portion, and
a third opening portion formed in the bottom portion to face a light receiving lens of a light receiving unit, the light receiving unit being configured to perform a predetermined process on received light, and
wherein the reflection member guides light coming from the irradiation region and being reflected by the inner surface to the light receiving lens; and
a light condensing lens between the second opening portion of the reflection member and the light receiving lens, and
wherein a concave lens is formed on a surface of the light condensing lens facing the light receiving lens and a convex lens is formed on a surface of the light condensing lens facing the second opening portion.

15. The light condensing unit according to claim 14, wherein the concave lens has a curvature greater than a curvature of the convex lens.

16. The light condensing unit according to claim 14, wherein the reflection member has an inner shape formed in a manner that an angle of incidence of light coming from the irradiation region on the light receiving lens is less than or equal to an angle that is three degrees greater than a converging angle of the light receiving lens.

17. The light condensing unit according to claim 14, wherein the reflection member has an inner shape formed in a manner that an angle of incidence of light coming from the irradiation region on the light receiving lens is less than or equal to a converging angle of the light receiving lens.

18. The light condensing unit according to claim 14, wherein the plurality of light irradiation members are arranged around the outer wall of the reflection member at substantially equal intervals from each other, and
wherein the plurality of light irradiation members have optical axes intersecting with each other substantially at a center of the irradiation region.

19. The light condensing unit according to claim 14, further comprising:
a housing formed by a light shielding member, the housing having an inner space for accommodating the reflection member and the light irradiation members, wherein the housing has an opening portion formed at each position corresponding to the second opening portion and the third opening portion of the reflection member.

20. The light condensing unit according to claim 19, wherein the housing is formed integrally with the light receiving unit.

21. The light condensing module according to claim 14, wherein a measurement target object is placed on the irradiation region, the measurement target object being at least a part of a living body, and
wherein the light irradiation member irradiates the measurement target object with light.

22. The light condensing unit according to claim 14, wherein the light receiving unit is an image sensor module configured to output a pixel signal depending on an amount of received light.

23. The light condensing unit according to claim 22, wherein an optical spectrum of light coming from the irradiation region is calculated based on the pixel signal outputted from the image sensor module.

24. The light condensing unit according to claim 14, wherein the first opening portion is a slit formed in a direction from the top portion of the reflection member toward the bottom portion of the reflection member.

25. The light condensing unit according to claim 14, wherein three or more of the light irradiation members are provided.

26. The light condensing unit according to claim 14, wherein the light irradiation member has an light emitting diode (LED) that emits white light.

27. A light detection system, comprising:
an image sensor module provided with a light receiving lens and configured to output a pixel signal depending on an amount of received light through the light receiving lens; and
a light condensing unit configured to condense light on the light receiving lens,
wherein the light condensing unit includes
a reflection member having a hollow dome shape, a side wall of the dome shape being curved to be extended from a top portion toward a bottom portion, the reflection member having a mirror-finished inner surface,
a plurality of light irradiation members arranged around an outer wall of the reflection member and configured to irradiate an irradiation region of the top portion with light through a first opening portion formed in the outer wall,
wherein the reflection member includes
a second opening portion formed in the irradiation region of the top portion, and
a third opening portion formed in the bottom portion to face a light receiving lens of a light receiving unit, the light receiving unit being configured to perform a predetermined process on received light, and
wherein the reflection member guides light coming from the irradiation region and being reflected by the inner surface to the light receiving lens, and
a collimating lens between the second opening portion of the reflection member and the light receiving lens, and
wherein the collimating lens and the light receiving lens constitute a collimator configured to correct light coming from the irradiation region and being reflected by the inner surface of the reflection member to produce parallel light.

28. A light detection system, comprising:
an image sensor module provided with a light receiving lens and configured to output a pixel signal depending on an amount of received light through the light receiving lens; and
a light condensing unit configured to condense light on the light receiving lens,
wherein the light condensing unit includes
a reflection member having a hollow dome shape, a side wall of the dome shape being curved to be extended from a top portion toward a bottom portion, the reflection member having a mirror-finished inner surface,
a plurality of light irradiation members arranged around an outer wall of the reflection member and configured to irradiate an irradiation region of the top portion with light through a first opening portion formed in the outer wall,
wherein the reflection member includes
a second opening portion formed in the irradiation region of the top portion, and
a third opening portion formed in the bottom portion to face a light receiving lens of a light receiving unit, the light receiving unit being configured to perform a predetermined process on received light, and
wherein the reflection member guides light coming from the irradiation region and being reflected by the inner surface to the light receiving lens, and
a light condensing lens between the second opening portion of the reflection member and the light receiving lens, and
wherein a concave lens is formed on a surface of the light condensing lens facing the light receiving lens and a convex lens is formed on a surface of the light condensing lens facing the second opening portion.

* * * * *